US010184877B2

(12) United States Patent
Hashimoto et al.

(10) Patent No.: US 10,184,877 B2
(45) Date of Patent: *Jan. 22, 2019

(54) SAMPLE FEEDING APPARATUS, FLOW CYTOMETER, AND SAMPLE FEEDING METHOD

(71) Applicant: Sony Corporation, Tokyo (JP)

(72) Inventors: Gakuji Hashimoto, Kanagawa (JP); Takayuki Kato, Chiba (JP)

(73) Assignee: Sony Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/423,088

(22) Filed: Feb. 2, 2017

(65) Prior Publication Data

US 2017/0146444 A1    May 25, 2017

Related U.S. Application Data

(63) Continuation of application No. 13/888,056, filed on May 6, 2013, now Pat. No. 9,606,025.

(30) Foreign Application Priority Data

May 17, 2012    (JP) .................................. 2012-113605

(51) Int. Cl.
*G01N 1/00*        (2006.01)
*G01N 15/00*       (2006.01)
(Continued)

(52) U.S. Cl.
CPC ........... *G01N 15/1404* (2013.01); *G01N 1/00* (2013.01); *G01N 15/00* (2013.01); *G01N 35/1095* (2013.01)

(58) Field of Classification Search
CPC combination set(s) only.
See application file for complete search history.

(56) References Cited

U.S. PATENT DOCUMENTS

| 4,462,963 A | 7/1984 | O'Brien et al. |
| 5,147,551 A | 9/1992 | Averette |

(Continued)

FOREIGN PATENT DOCUMENTS

| CN | 102334021 | 1/2012 |
| JP | 51-113690 | 10/1976 |

(Continued)

OTHER PUBLICATIONS

Japanese Office Action dated Nov. 7, 2017 in corresponding Japanese Application No. 2016-084987.

(Continued)

*Primary Examiner* — Brian R Gordon
(74) *Attorney, Agent, or Firm* — K&L Gates LLP

(57) ABSTRACT

A sample feeding apparatus includes a first cylinder, a second cylinder, and a sealing section. The first cylinder is configured to be mounted with a sample tube. The second cylinder is configured to move the first cylinder between a first position and a second position, the first position being for mounting of the sample tube, the second position being for feeding of a sample in the sample tube. The sealing section is configured to cover the sample tube, the sample tube being mounted to the first cylinder being at the second position, the first cylinder applying pressure to an inner space of the sealing section at the second position.

4 Claims, 19 Drawing Sheets

(51) Int. Cl.
*G01N 15/14* (2006.01)
*G01N 35/10* (2006.01)

(56) References Cited

U.S. PATENT DOCUMENTS

| 6,473,171 B1 | 10/2002 | Buttry et al. |
| 2012/0225000 A1 | 9/2012 | Ford |

FOREIGN PATENT DOCUMENTS

| JP | 04-015540 | 9/1983 |
| JP | 62-187183 | 12/1987 |
| JP | 1-91800 | 6/1989 |
| JP | 04-500732 | 7/1990 |
| JP | 11-083804 | 3/1999 |
| JP | 2001-311736 | 11/2001 |
| JP | 2006-029868 | 2/2006 |
| JP | 2006-322896 | 11/2006 |
| JP | 2007-147516 | 6/2007 |
| JP | 2008-039405 | 2/2008 |
| JP | 2009-121846 | 6/2009 |
| JP | 2010-133843 | 6/2010 |
| JP | 2010-286292 | 12/2010 |

OTHER PUBLICATIONS

Office Action received in JP Application 2012113605, dated Dec. 1, 2015 (6 pages).
Chinese Office Action dated Mar. 25, 2016 in corresponding Chinese Application No. 2013101737877.
Japanese Office Action dated Mar. 14, 2017 in corresponding Japanese Application No. 2016-084987.
Chinese Office Action dated Dec. 12, 2016 in corresponding Chinese Application No. 201310173787.7.
Japanese Office Action dated Jun. 5, 2018 in corresponding Japanese Application No. 2016-084987.

SAMPLE FEEDING APPARATUS, FLOW CYTOMETER, AND SAMPLE FEEDING METHOD

CROSS REFERENCES TO RELATED APPLICATIONS

The present application is a continuation application of U.S. patent application Ser. No. 13/888,056, filed on May 6, 2013, which application claims priority to Japanese Priority Patent Application JP 2012-113605 filed in the Japan Patent Office on May 17, 2012, the entire content of which is hereby incorporated by reference.

BACKGROUND

The present disclosure relates to a sample feeding apparatus, a flow cytometer, and a sample feeding method. More specifically, the present disclosure relates to a sample feeding apparatus and others that feed a sample to a micro-sized particle measurement apparatus.

There is known a micro-sized particle measurement apparatus, e.g., flow cytometer, that optically, electrically, or magnetically detects properties of micro-sized particles such as cells. The micro-sized particle measurement apparatus then separates and collects only the micro-sized particles having any predetermined properties.

With this micro-sized particle measurement apparatus, a sample possible for use is bio-related micro-sized particles exemplified by cells, microorganisms, and liposomes. As an example, see Japanese Patent Application Laid-open No. 2010-286292. The sample as such is expected not to adhere to the body of a user for safety, for example. There thus is expected to pay attention to handle the sample at the time of feeding to the micro-sized particle measurement apparatus using a sample feeding apparatus (or a sample feeding apparatus configured as a part of the micro-sized particle measurement apparatus).

SUMMARY

The concern here is that, at the time of feeding of the sample, a previous sample feeding apparatus is expected to apply very strong forces to components for pressurization thereon using a cylinder. Considering the very strong forces to be applied on the components in the apparatus as such, the user has to be careful not to get his fingers caught in the cylinder and others, or a sample tube has to be protected from damage. In order to handle the apparatus with safety, the user has been expected to be technically skilled, and this has been annoying the user. There thus has been a demand for a sample feeding apparatus that is capable of sample feeding with safety and ease.

It is thus desirable to provide a sample feeding apparatus, a flow cytometer, and a sample feeding method with which sample feeding is performed with safety and ease.

According to an embodiment of the present disclosure, there is provided a sample feeding apparatus, including a first cylinder, a second cylinder, and a sealing section. The first cylinder is configured to be mounted with a sample tube. The second cylinder is configured to move the first cylinder between a first position and a second position, the first position being for mounting of the sample tube, the second position being for feeding of a sample in the sample tube. The sealing section is configured to cover the sample tube, the sample tube being mounted to the first cylinder being at the second position, the first cylinder applying pressure to an inner space of the sealing section at the second position.

This sample feeding apparatus may further include a third cylinder that is configured to be mounted to support the first cylinder in a state that the first cylinder is positioned at the second position.

In this sample feeding apparatus, the third cylinder may be configured to support the first cylinder by moving from a third position to a fourth position, the third position allowing the first cylinder to move between the first position and the second position, the fourth position being on an opposite side of the sealing section with respect to the first cylinder.

This sample feeding apparatus may further include a fourth cylinder that is configured to be mounted to accommodate any of the sample remained in the sealing section in a state that the first cylinder is positioned at the first position.

In this sample feeding apparatus, the fourth cylinder may be configured to accommodate the sample remained in the sealing section by moving from a fifth position to a sixth position, the fifth position allowing the first cylinder to move between the first position and the second position, the sixth position being on an insertion side of the sample tube with respect to the sealing section.

In this sample feeding apparatus, each of the first cylinder, the second cylinder, the third cylinder, and the fourth cylinder may include a flow path that is configured to move gas for injection into the cylinder, and a valve that is configured to draw in and out the gas in the other cylinders via the flow path based on an operation of the cylinder.

This sample feeding apparatus may further include a control unit that is configured to inject the gas into the fourth cylinder. The fourth cylinder may include a first valve that is configured to physically open itself in response to the fourth cylinder moving from the sixth position to the fifth position by the injection of the gas thereinto, and to allow the gas to be injected into the second cylinder to move the second cylinder from the first position to the second position.

In this sample feeding apparatus, the sealing section may be configured to allow the injection of the gas into the inner space thereof by the opening of the first valve.

In this sample feeding apparatus, the second cylinder may include a second valve that is configured to physically open itself to allow the gas to be injected into the third cylinder in a state that the second cylinder is positioned at the second position, and to allow the third cylinder to move from the third position to the fourth position.

In this sample feeding apparatus, the third cylinder may include a third valve that is configured to physically open itself to allow the gas to be injected into the first cylinder in a state that the third cylinder is positioned at the fourth position, and to allow the first cylinder to apply pressure into the sealing section at the second position.

In this sample feeding apparatus, the control unit may be configured to perform the injection of the gas into the first cylinder and the third cylinder. The third cylinder may include a fourth valve that is configured to physically open itself in response to the third cylinder moving from the fourth position to the third position by the injection of the gas thereinto, and to allow the second cylinder to move from the second position to the first position.

In this sample feeding apparatus, by the control unit injecting the gas into the first cylinder, the pressure applied by the first cylinder into the sealing section may be released.

In this sample feeding apparatus, the second cylinder may include a fifth valve that is configured to physically open itself to allow the gas to be injected into the fourth cylinder in a state that the second cylinder is positioned at the first position, and to allow the fourth cylinder to move from the fifth position to the sixth position.

In this sample feeding apparatus, the sealing section may be attached with a sample line that is configured to feed the sample in the sample tube to an outside.

According to another embodiment of the present disclosure, there is provided a flow cytometer that is coupled with the sample feeding apparatus described above.

According to still another embodiment of the present disclosure, there is provided a sample feeding method for a sample feeding apparatus, the method including: moving a first cylinder that is mounted with a sample tube at a first position to a second position at which a sealing section covers over the first cylinder by using a second cylinder; and applying pressure to an inner space of the sealing section by the first cylinder.

The sample feeding method may further include supporting, in a state that the first cylinder is positioned at the second position, the first cylinder by moving a third cylinder from a third position to a fourth position, the third position allowing the first cylinder to move between the first position and the second position, the fourth position being on an opposite side of the sealing section with respect to the first cylinder.

The sample feeding method may further include using the second cylinder to move the first cylinder from the second position to the first position.

The sample feeding method may further include accommodating, in a state that the first cylinder is positioned at the first position, any of the sample remained in the sealing section by moving a fourth cylinder from a fifth position to a sixth position, the fifth position allowing the first cylinder to move between the first position and the second position, the sixth position being on an insertion side of the sample tube with respect to the sealing section.

The sample feeding method may further include starting an operation of each of the first cylinder, the second cylinder, the third cylinder, and the fourth cylinder in response to a gas flow via a flow path to the other cylinders by opening of a valve based on the operation of each of the cylinders.

In this disclosure, the "sample" is exemplified by a sample mainly including micro-sized particles.

The "micro-sized particles" may widely include bio-related micro-sized particles such as cells, microorganisms, and liposomes, or synthetic particles such as latex particles, gel particles, and industrial particles.

The bio-related micro-sized particles include chromosomes found in various types of cells, liposomes, mitochondrias, organelles, and others. The cells include animal cells, e.g., hematopoietic cells, and plant cells. The microorganisms include bacteria such as *Escherichia coli*, virus such as tobacco mosaic virus, fungi such as yeast, and others. The bio-related micro-sized particles may also include bio-related macromolecules such as nucleic acids, proteins, and composites thereof, and others. The industrial particles may include organic or inorganic polymeric materials, metal, and others. The organic polymeric materials include polystyrene, styrene-divinylbenzene, polymethyl methacrylate, and others. The inorganic polymeric materials include glass, silica, magnetic materials, and others. The metal includes gold collide, aluminum, and others. These micro-sized particles are generally spherical in shape, but may be non-spherical and not specifically restricted in size and mass, for example.

This disclosure achieves sample feeding with safety and ease.

These and other objects, features and advantages of the present disclosure will become more apparent in light of the following detailed description of best mode embodiments thereof, as illustrated in the accompanying drawings.

Additional features and advantages are described herein, and will be apparent from the following Detailed Description and the figures.

DETAILED DESCRIPTION

Hereinafter, a suitable embodiment of the present disclosure will be described with reference to the drawings. The following embodiment is no more than an example of a typical embodiment of the present disclosure, and this may not narrow the scope of the present disclosure. The description is given in the following order.

Figure 1:
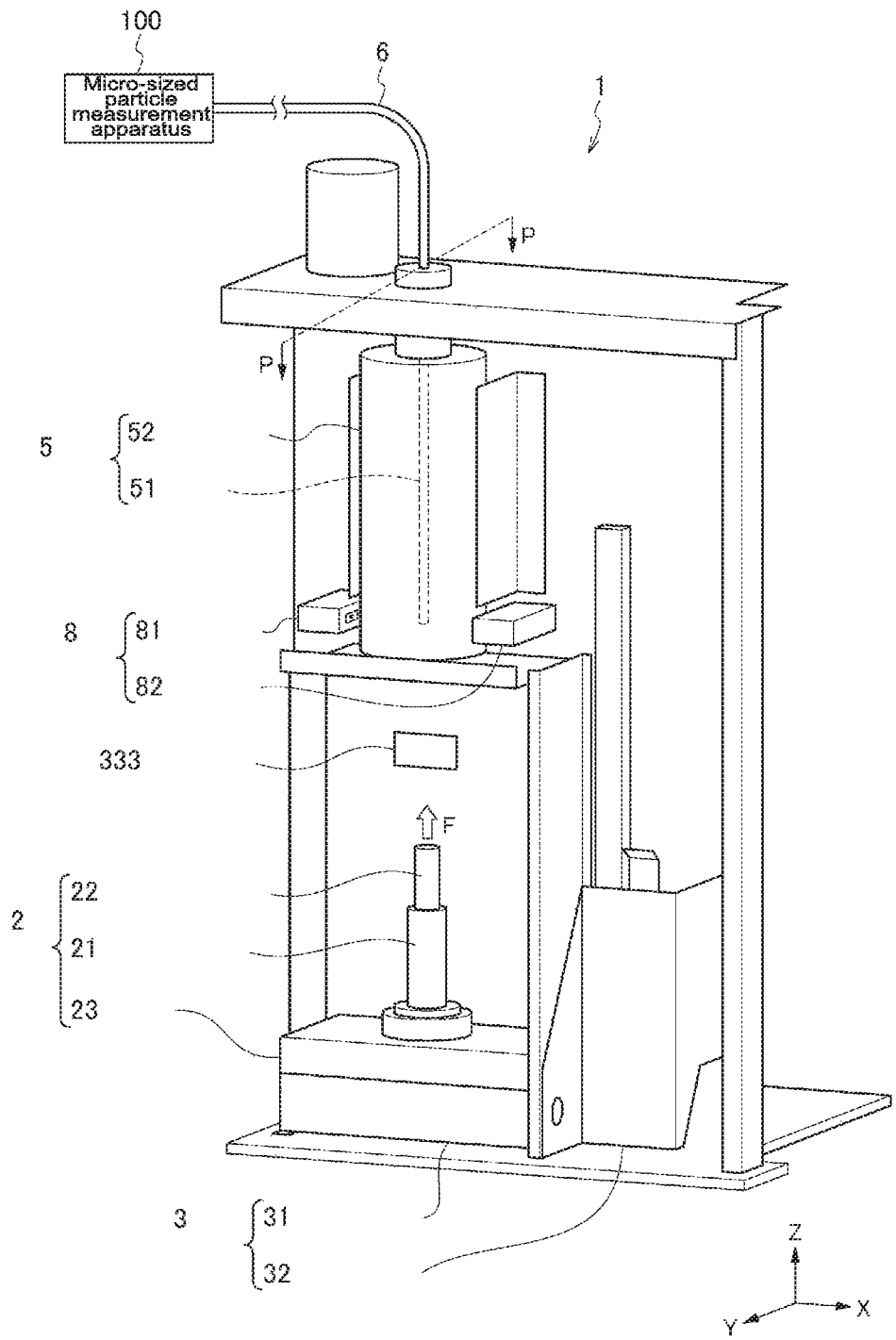
FIG. 1 is a perspective diagram illustrating the entire configuration of a sample feeding apparatus according to an embodiment of the present disclosure.
Figure 2:
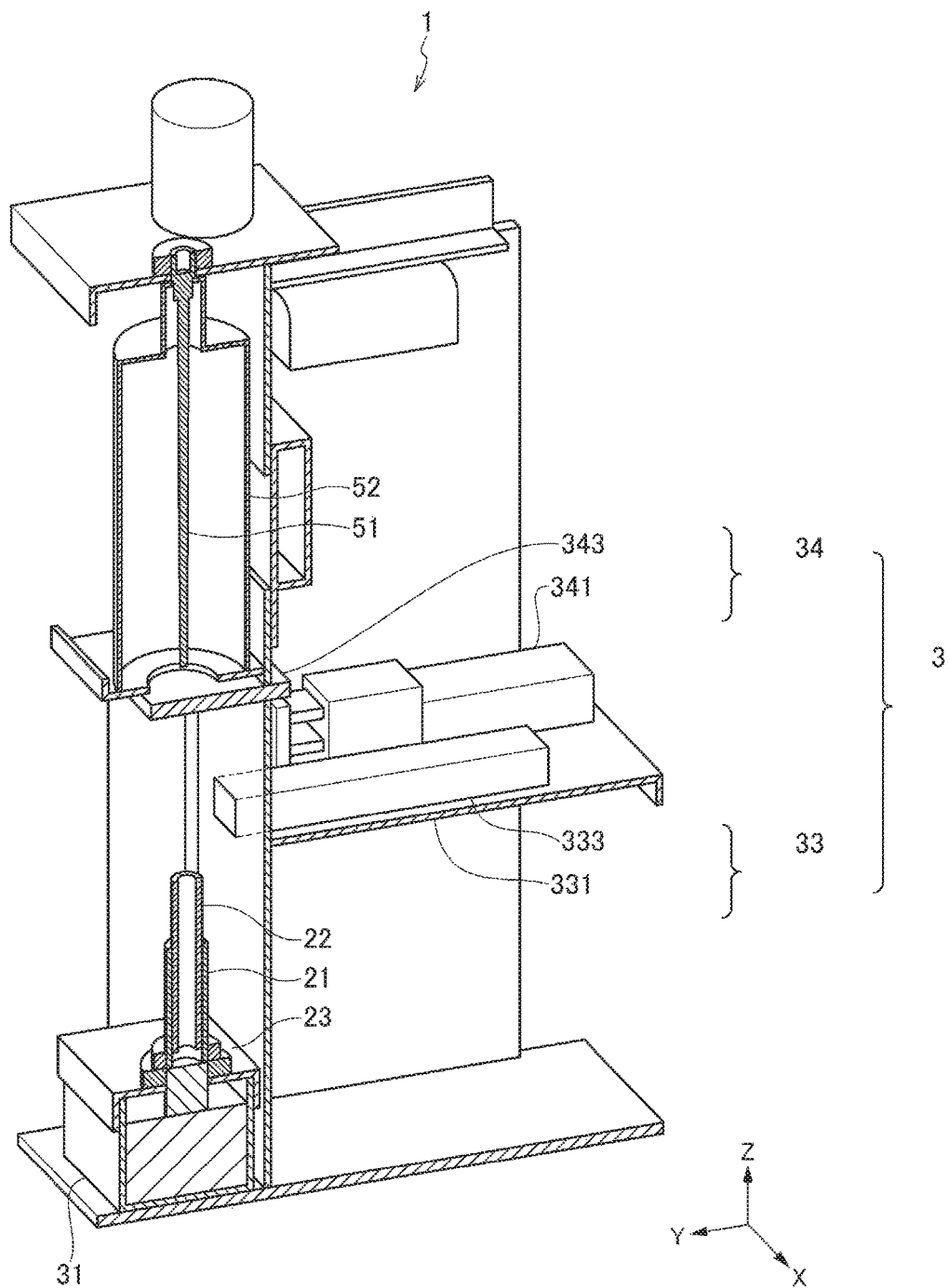
FIG. 2 is a cross-sectional schematic diagram illustrating the entire configuration of the sample feeding apparatus according to the embodiment of the present disclosure.
Figure 3:
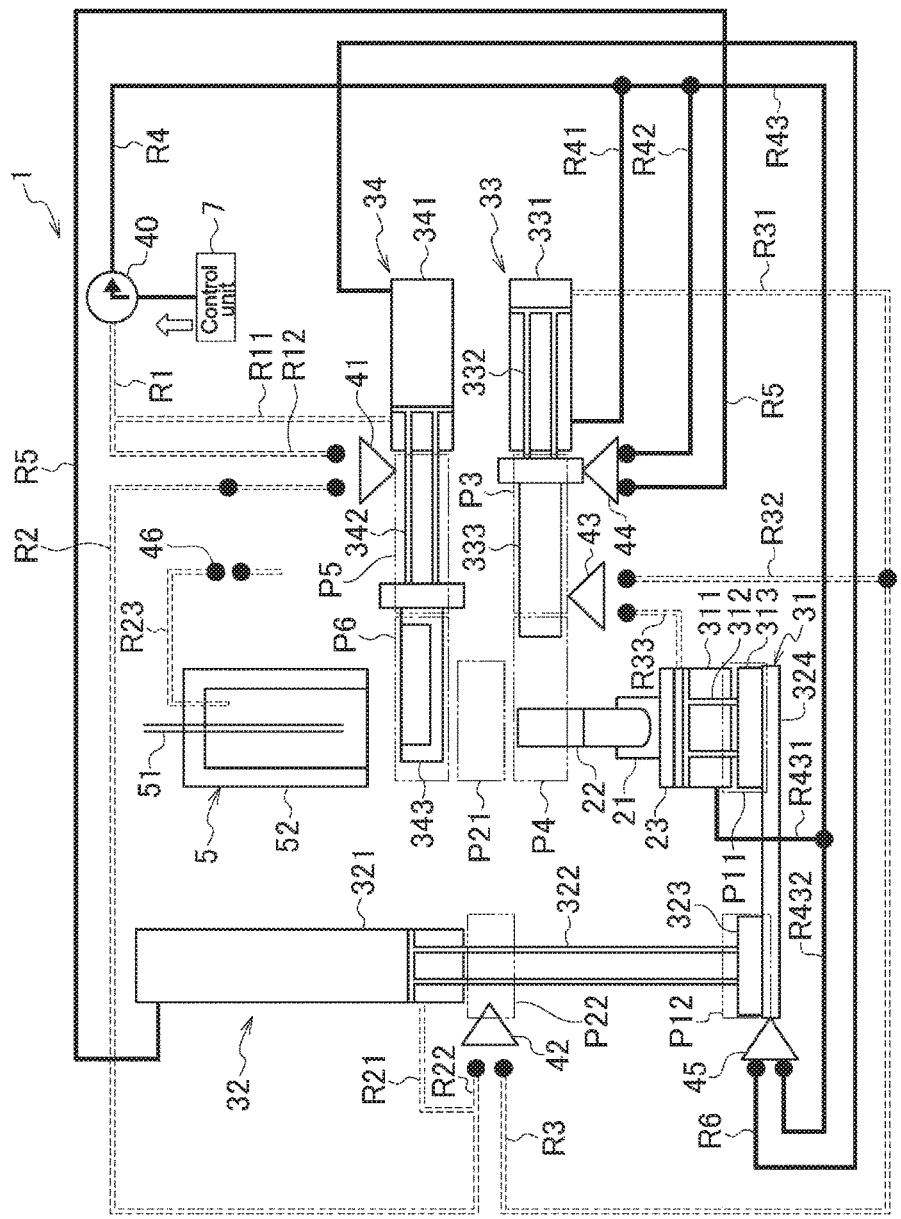
FIG. 3 is a sequential-structure diagram illustrating the entire configuration of the sample feeding apparatus according to the embodiment of the present disclosure, and is a schematic diagram illustrating the sequential structure of the sample feeding apparatus in a step $S_1$ of sample setting wait in a sample feeding method according to another embodiment of the present disclosure.
Figure 4:
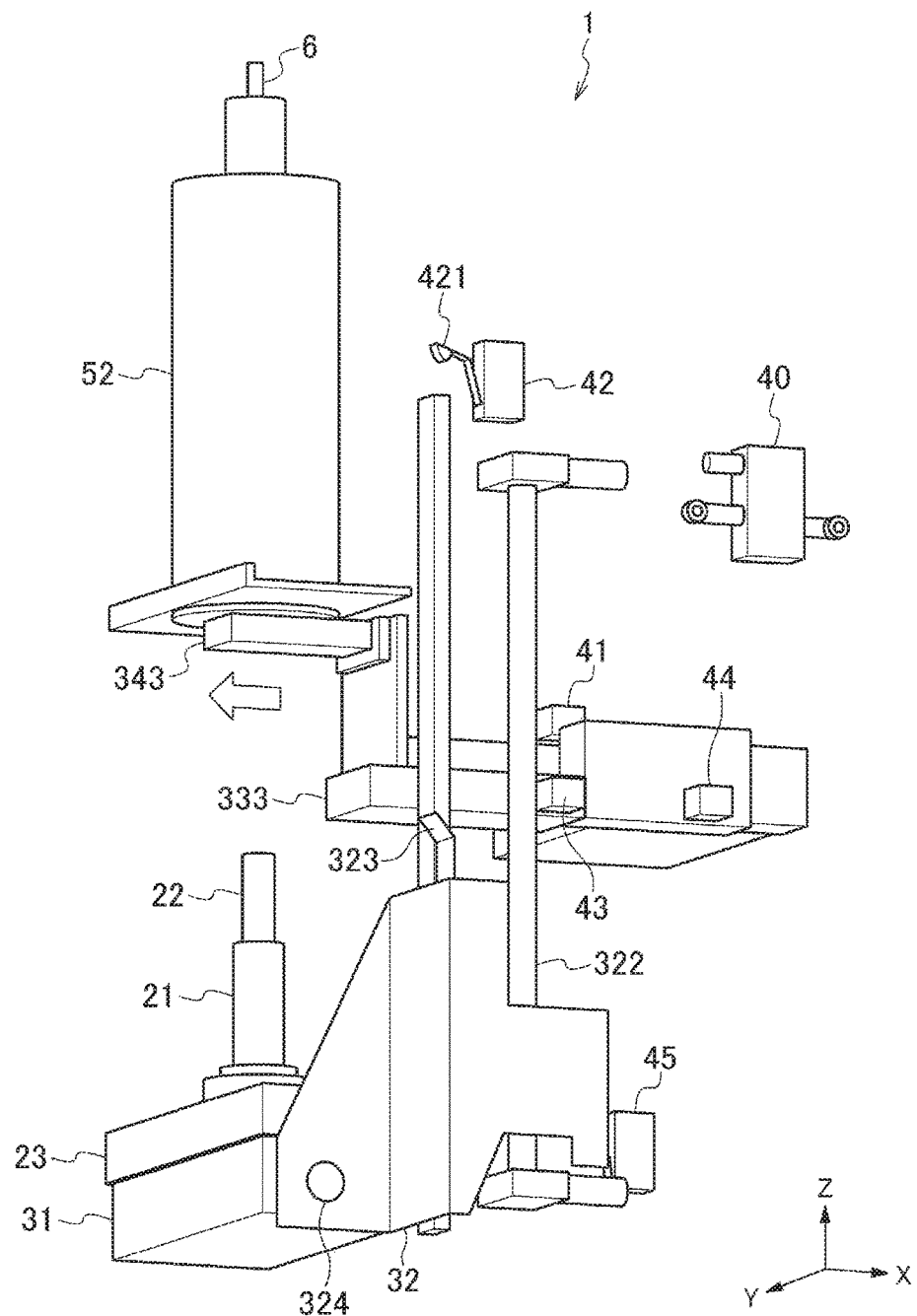
FIG. 4 is a perspective diagram illustrating the entire configuration of the sample feeding apparatus according to the embodiment of the present disclosure, and is a schematic diagram illustrating in what state the sample feeding apparatus is in the sample-setting-wait step $S_1$ in the sample feeding method according to the embodiment of the present disclosure.

1. Structure of Sample Feeding Apparatus 1 according to Embodiment of Present Disclosure
    1-1. Stirring Unit
    1-2. Air Cylinder
        1-2-1. Pressure Cylinder
        1-2-2. Up-and-down Cylinder
        1-2-3. Support Cylinder
        1-2-4. Waste-containing Cylinder
    1-3. Valve and Flow Path
    1-4. Pressure Feeding Section
    1-5. Sample Line
    1-6. Control Unit 7, and Others
2. Sample Feeding Method according to Embodiment of Present Disclosure
    2-1. Sample-setting-wait Step $S_1$
    2-2. Waste-tray-storage Step $S_2$
    2-3. Pressure-cylinder-moving-up Step $S_3$
    2-4. Support-arm-protrusion Step $S_4$
    2-5. Sample-feeding Step $S_5$
    2-6. Pressure-cylinder-release Step $S_6$
    2-7. Pressure-cylinder-moving-down Step $S_7$
    2-8. Waste-tray-protrusion Step $S_8$ 1. Structure of Sample Feeding Apparatus 1 According to Embodiment of Present Disclosure FIG. 1 is a schematic diagram illustrating the configuration of a sample feeding apparatus 1 according to an embodiment of the present disclosure. The sample feeding apparatus 1 is configured as a sample loading module. FIG. 2 is a cross-sectional schematic diagram illustrating the entire configuration of the sample feeding apparatus 1, and is a cross-sectional diagram cut along a line P-P of FIG. 1. FIG. 3 is a sequential-structure diagram illustrating the entire configuration of the sample feeding apparatus 1. FIG. 4 is also a schematic diagram illustrating the entire configuration of the sample feeding apparatus 1 according to the embodiment of the present disclosure.

1-1. Stirring Unit

In FIG. 1, a reference numeral 2 denotes a stirring unit 2 that stirs a sample in a sample tube 22 in place. The stirring unit 2 includes a tube holder 21, and a base 23. The tube holder 21 houses therein the sample tube 22, and the base 23 carries thereon the tube holder 21. In addition to the tube holder 21 and the base 23, the stirring unit 2 may include a motor (not shown) that rotates the tube holder 21 to stir the sample in the sample tube 22.

The sample tube 22 is not specifically restricted as long as the sample tube contains the sample, but is desirably exemplified by an eppendorf tube or a conical tube. The motor (not shown) is exemplified by a rotation device including a stepping motor, for example.

1-2. Air Cylinder

In FIG. 1, a reference numeral 3 denotes an air cylinder that allows feeding of the sample in the sample tube 22 to a micro-sized particle measurement apparatus 1 and others. For the sample feeding, the air cylinder moves upward, i.e., in the direction of an arrow F of FIG. 1 (in the Z-axis positive direction), the stirring unit 2 so as to place the sample tube 22 in a pressure feeding section 5. This air cylinder 3 includes a pressure cylinder 31, and an up-and-down cylinder 32. The pressure cylinder 31 applies pressure to the stirring unit 2 to keep the stirring unit gas-tight, and the up-and-down cylinder 32 moves up and down the pressure cylinder 31 in the Z-axis direction. By moving the tube holder 21 in the stirring unit 2 up into the pressure feeding section 5, the sample in the sample tube 22 may be directed to the micro-sized particle measurement apparatus, and others.

The air cylinder 3 also includes a support cylinder 33, and a waste-containing cylinder 34 (see FIG. 2). The support cylinder 33 supports the pressure cylinder 31 at the time of feeding of the sample, and the waste-containing cylinder 34 accommodates any sample remained in a pressure shell 52 in the pressure feeding section 5 that will be described later.

1-2-1. Pressure Cylinder

The pressure cylinder 31 of FIG. 1 is an example of a first cylinder according to the embodiment of the present disclosure. The pressure cylinder 31 includes a pressure cylinder body section 311, and a pressure-cylinder-use piston 312 (see FIG. 3). The pressure cylinder body section 311 is mounted with the sample tube 22, and into the pressure cylinder body section 311, gas may be injected. The pressure-cylinder-use piston 312 allows the pressure cylinder body section 311 to move by the gas injection thereinto. The pressure cylinder 31 also includes a pressure-cylinder-use leg section 313 that is coupled to the up-and-down cylinder 32 that will be described later.

1-2-2. Up-and-Down Cylinder

The up-and-down cylinder 32 of FIG. 1 is an example of a second cylinder according to the embodiment of the present disclosure. The up-and-down cylinder 32 includes an up-and-down cylinder body section 321, an up-and-down-cylinder-use piston 322, and an up-and-down-cylinder-use leg section 323 (see FIG. 3). Into the up-and-down cylinder body section 321, gas may be injected. The up-and-down-cylinder-use piston 322 is allowed to move by the gas injection into the up-and-down cylinder body section 321. The up-and-down-cylinder-use leg section 323 is coupled to the pressure cylinder 31. The up-and-down cylinder 32 also includes a coupling section 324 that couples together the up-and-down-cylinder-use leg section 323 and the pressure-cylinder-use leg section 313.

In response to the gas injection into the up-and-down cylinder body section 321, both the pressure-cylinder-use leg section 313 and the up-and-down-cylinder-use leg section 323 are allowed to move between two positions. That is, at the one position, the sample tube 22 is mounted to the pressure cylinder 31 (hereinafter, this position may be sometimes referred to as first position P12 (see FIG. 3)), and at the other position, the sample tube 22 is housed in the pressure shell 52 that will be described later (hereinafter, this position may be sometimes referred to as second position P22 (see FIG. 3)). That is, the pressure-cylinder-use leg section 313 and the up-and-down-cylinder-use leg section 323 are allowed to move in the Z-axis direction of FIG. 1.

1-2-3. Support Cylinder

The support cylinder 33 of FIG. 2 is an example of a third cylinder according to the embodiment of the present disclosure. The support cylinder 33 includes a support cylinder body section 331, a support-cylinder-use piston 332, and a support arm 333 (see FIGS. 2 and 3). Into the support cylinder body section 331, gas may be injected. The support-cylinder-use piston 332 is allowed to move by the gas injection into the support cylinder body section 331. The support arm 333 may support the pressure cylinder 31.

When the pressure-cylinder-use leg section 313 in the pressure cylinder 31 is positioned at the second position P21 (see FIG. 3), the support arm 333 may support the pressure cylinder 31 by moving from one position to the other position. The one position is between the first position P11 (FIG. 3) and the second position P21 at which the pressure-cylinder-use leg position 313 is allowed to move (hereinafter, this position may be sometimes referred to as third position P3), and the other position is on the opposite side of the pressure feeding section 5 with respect to the first cylinder (hereinafter, this position may be sometimes referred to as fourth position P4). That is, the support arm 333 moves in the Y-axis positive direction of FIG. 2 to support the pressure cylinder 31.

With the support arm 333 supporting the pressure cylinder 31 at the fourth position P4, the pressure cylinder 31 is allowed to apply pressure into the pressure shell 52.

In the pressure cylinder 33, the support arm 333 may be moved from the fourth position P4 to the third position P3 in advance before the movement of the pressure cylinder 31, i.e., the movement of the pressure-cylinder-use leg section 313 from the second position P21 to the first position P11.

1-2-4. Waste-Containing Cylinder

The waste-containing cylinder 34 of FIG. 2 is an example of a fourth cylinder according to the embodiment of the present disclosure. The waste-containing cylinder 34 includes a waste-containing cylinder body section 341, a waste-cylinder-use piston 342, and a waste tray 343 (see FIGS. 2 and 3). Into the waste-containing cylinder body section 341, gas may be injected. The waste-cylinder-use piston 342 is allowed to move by the gas injection into the waste-containing cylinder body section 341. The waste tray 343 may collect any sample remained in the pressure shell 52 that will be described later.

When the pressure-cylinder-use leg section 313 in the pressure cylinder 31 is positioned at the first position P11, the waste tray 343 may move from one position to the other position to accommodate any sample remained in the pressure shell 52. That is, the one position is between the first position P11 and the second position P21 at which the first cylinder is allowed to move (hereinafter, this position may be sometimes referred to as fifth position P5), and the other position is on the insertion side of the sample tube 22 with respect to the pressure shell 52 (hereinafter, this position may be sometimes referred to as sixth position P6). Herein, the insertion side of the sample tube 22 is on the side in the Z-axis negative direction of FIG. 2.

With the waste tray 343 collecting any waste in the pressure shell 52 at the sixth position P6, the user may make preparation with safety for the sample tube 22 in the sample feeding apparatus 1 without worrying about the sample attaching to his hands and others.

In the waste-containing cylinder 34, the waste tray 343 may be moved from the sixth position P6 to the fifth position P5 in advance before the movement of the pressure cylinder 31, i.e., the movement of the pressure-cylinder-use leg section 313 from the second position P21 to the first position P11.

1-3. Valve and Flow Path

In FIG. 3, reference numerals 40 to 46 respectively denote valves that control gas injection into the air cylinder 3, i.e., the pressure cylinder 31, the up-and-down cylinder 32, the support cylinder 33, and the waste-containing cylinder 34.

Among these valves, the reference numeral 40 of FIG. 3 denotes an electromagnetic valve that is under the operation control of a control unit 7 that will be described later. Opening this electromagnetic valve allows gas to flow into the waste-containing cylinder 34, or into the pressure cylinder 31 and the support cylinder 33.

In FIGS. 3 and 4, the reference numerals 41 to 45 respectively denote mechanical valves that physically open themselves based on the operation of the air cylinder 3, i.e., the pressure cylinder 31, the up-and-down cylinder 32, the support cylinder 33, and the waste-containing cylinder 34. By the mechanical valves physically opening themselves, the gas in the appropriate cylinders is drawn in and out.

The mechanical valve 41 of FIG. 3 is an example of a first valve according to the embodiment of the present disclosure. The mechanical valve 41 is provided to the waste-containing cylinder 34. The mechanical valve 41 physically opens itself by the waste tray 343 moving from the sixth position P6 to the fifth position P5 in response to injection of gas into the waste-containing cylinder body section 341 via a flow path R1.

With the opening of the mechanical valve 41, the gas is injected into the up-and-down cylinder body section 321 via a flow path R2 so that both the up-and-down-cylinder-use leg section 323 and the pressure-cylinder-use leg section 313 are allowed to move from the first positions P11 and P12 to the second positions P21 and P22, respectively.

The opening of the mechanical valve 41 may also open an air-operated valve 46 so that gas injection is allowed into the pressure shell 52.

As will be described later, FIG. 3 is a diagram showing in what state the sample feeding apparatus 1 is in the sample-setting-wait step $S_1$ in the sample feeding method. In FIG. 3, the mechanical valve 41 is not coupled with flow paths R12 and R2 that will be described later. That is, in the drawing, the triangle mark is not in contact with circular marks at the end of the flow paths. This means that the mechanical valve 41 is not open, and thus the gas is not allowed to flow. This is applicable also to other drawings. On the other hand, the mechanical valve 44 that will be described later is coupled with flow paths R42 and R5 that will be described later. That is, in the drawing, the triangle mark is in contact with circular marks at the end of the flow paths. This means that the mechanical valve 44 is open, and thus the gas is allowed to flow. This is applicable also to other drawings.

The mechanical valve 42 of FIG. 3 is an example of a second valve according to the embodiment of the present disclosure. The mechanical valve 42 is provided to the up-and-down cylinder 32. The mechanical valve 42 physically opens itself when the up-and-down-cylinder-use leg section 323 in the up-and-down cylinder 32 is positioned at the second position P22. To be specific, the mechanical valve 42 opens itself by a switch section 421 therein being pushed by the up-and-down-cylinder-use leg section 323 (see also FIG. 9 that will be described later). Herein, the remaining mechanical valves 41, 43, 44, and 45 share substantially the same opening structure and function with the mechanical valve 42. Therefore, these mechanical valves 41, 43, 44, and 45 are not described again about their opening.

With the mechanical valve 42 opening itself, gas is injected into the support cylinder body section 331 via a flow path R3 so that the support arm 333 is allowed to move from the third position P3 to the fourth position P4.

The mechanical valve 43 of FIG. 3 is an example of a third valve according to the embodiment of the present disclosure. The mechanical valve 43 is provided to the support cylinder 33. The mechanical valve 43 physically opens itself when the support arm 333 is positioned at the fourth position P4.

With the opening of the mechanical valve 43, the gas is injected into the pressure cylinder body section 311 via a flow path R33 so that the pressure cylinder 31 is allowed to apply pressure into the pressure shell 52 when the pressure-cylinder-use leg section 313 is positioned at the second position P21.

The mechanical valve 44 of FIG. 3 is an example of a fourth valve according to the embodiment of the present disclosure. The mechanical valve 44 is provided to the support cylinder 33. In response to gas injection into the support cylinder body section 331 by the control unit 7 via a flow path R4, the mechanical valve 43 physically opens itself when the support arm 333 is positioned at the third position P3.

With the opening of the mechanical valve 44, the gas is injected into the up-and-down cylinder body section 321 via the flow path R5 so that the up-and-down-cylinder-use leg section 323 is allowed to move from the second position P22 to the first position P12.

The mechanical valve 45 of FIG. 3 is an example of a fifth valve according to the embodiment of the present disclosure. The mechanical valve 45 is provided to the up-and-down cylinder 32. The mechanical valve 45 physically opens itself when the up-and-down-cylinder use leg section 323 is positioned at the first position P12.

With the opening of the mechanical valve 45, the gas is injected into the waste-containing cylinder body section 341 via a flow path R6 so that the waste tray 343 is allowed to move from the fifth position P5 to the sixth position P6.

In FIG. 3, the reference numeral 46 denotes an air-operated valve that opens itself to allow gas injection into the pressure shell 52. With this air-operated valve, sequence control is enabled by a switch port operating in response to the pressure from a control port.

In FIG. 3, reference numerals R1, R11, R12, R2, R21, R22, R3, R31, R32, R33, R4, R41, R42, R43, R431, R432, R5, and R6 each denote a flow path that moves gas therethrough before injection into the air cylinder 3. A description will be given in detail later about which flow path moves the gas between which components when a description is given later about the sample feeding method according to the embodiment of the present disclosure. The flow paths are not specifically restricted as long as these paths allow the gas to flow therethrough. These flow paths are exemplified by tubes and others having various diameters based on the flow velocity and others of any desired gas.

As will be described later, FIG. 3 is a diagram showing in what state the sample feeding apparatus 1 is in the sample-setting-wait step $S_1$ in the sample feeding method. Among the flow paths of FIG. 3, the flow path R5 and others indicated by solid lines show that there is a gas flow therethrough. On the other hand, in FIG. 3, the flow paths R1, R2, and others indicated by broken lines show that there is no gas flow therethrough. This is applicable also to other drawings.

1-4. Pressure Feeding Section

In FIG. 1, a reference numeral 5 denotes a pressure feeding section that feeds the sample to a micro-sized particle measurement apparatus 100 and others while applying pressure to the sample. The pressure feeding section 5 is an example of a sealing section according to the embodiment of the present disclosure. The pressure feeding section 5 includes the pressure shell 52, and a nozzle 51. The pressure shell 52 is placed over the sample tube 22 when the sample tube is moved up in the Z-axis positive direction in response to the movement of the pressure-cylinder-use leg section 313 from the first position P11 to the second position P21. The nozzle 51 draws the sample by suction in the sample tube 22.

The pressure application by the pressure feeding section 5 is not specifically restricted as long as the sample in the sample tube 22 is fed thereby. The pressure feeding section 5 allows gas injection into the pressure shell 52 via the air-operated valve 46 and a flow path R23 by opening of the mechanical valve 41 (see FIG. 3).

The nozzle 51 functions as a stirring rod when stirring the sample so that the sample is stirred with a higher efficiency.

1-5. Sample Line

In FIG. 1, a reference numeral 6 denotes a sample line 6 that directs the sample in the sample tube 22 to the outside. This sample is the one fed with pressure application by the pressure feeding section 5 described above. The sample directed to the sample line 6 is fed to the micro-sized particle measurement apparatus (flow cytometer) 100, which is linked to the sample line 6. The sample line 6 is not specifically restricted, but is exemplarily configured by a silicone tube.

1-6. Control Unit, and Others

The sample feeding apparatus 1 may include the control unit 7 that may perform gas injection into the waste-containing cylinder body section 341 via the electromagnetic valve 40 and the flow path R1 (see FIG. 3). The control unit 7 may perform gas injection also into both the up-and-down cylinder body section 321 and the support cylinder body section 331 via the electromagnetic valve 40.

The control unit 7 may be configured by a general-purpose computer including a CPU (Central Processing Unit), a memory (storage section), a hard disk, and others. The hard disk stores an OS (Operating System), a program that runs to perform sample-making steps that will be described next, and others.

The sample feeding apparatus 1 also includes an operation section for the user to drive a data analysis section and the control unit 7, and others. In addition thereto, the sample feeding apparatus 1 may also include a level detection sensor 8 that detects the level of the sample in the sample tube 22 (see FIG. 1). This level detection sensor 8 includes a light irradiation section 81, and a light detection section 82. The light irradiation section 81 is in charge of light irradiation, and the light detection section 82 detects the light coming from the light irradiation section 81.

The sample feeding apparatus 1 may be provided with an output section that warns the user when the sample remained in the sample tube 22 is reduced down to a predetermined reference value, for example. The output section may warn the user in various manners, including using a lamp, displaying a message and others, outputting audio, and others.

In the present disclosure, the sample feeding apparatus 1 is described as an apparatus that feeds a sample to the micro-sized particle measurement apparatus (flow cytometer) 100 coupled thereto. Alternatively, the sample feeding apparatus 1 may be configured as a part of the micro-sized particle measurement apparatus 100.

Figure 5:
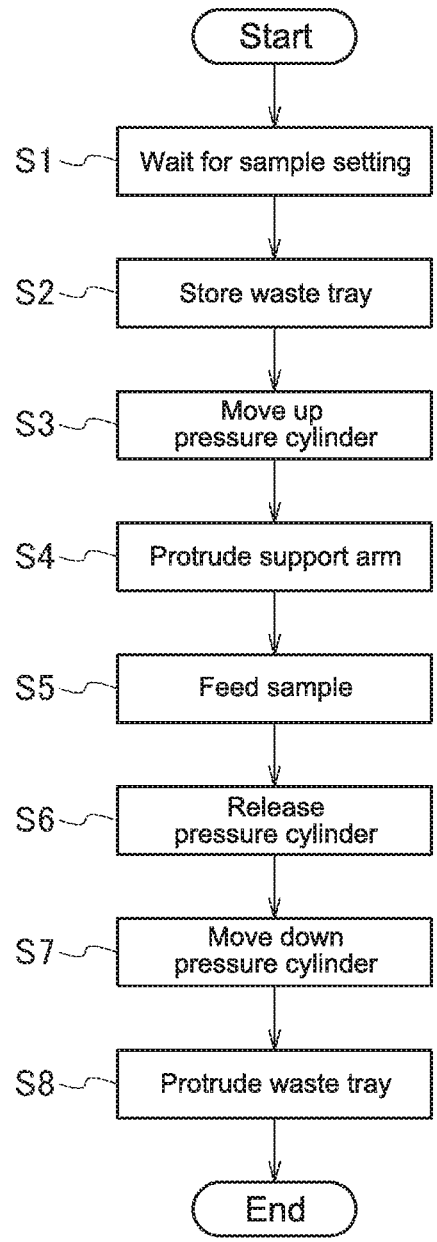
FIG. 5 is a flowchart illustrating the sample feeding method according to the embodiment of the present disclosure.

2. Sample Feeding Method According to Embodiment of Present Disclosure 2-1. Sample-Setting-Wait Step $S_1$ Described below is a sample feeding method according to an embodiment of the present disclosure by referring to FIGS. 3 to 19. FIGS. 3, 4, and 6 to 19 are each a schematic diagram showing in what state the sample feeding apparatus 1 is while performing the sample feeding method according to the embodiment of the present disclosure. The sample feeding method includes procedural steps of "sample-setting-wait step $S_1$", "waste-tray-storage step $S_2$", "pressure-cylinder-moving-up step $S_3$", "Support-arm-protrusion step $S_4$", "sample-feeding step $S_5$", "pressure-cylinder-release step $S_6$", "pressure-cylinder-moving-down step $S_7$", and "waste-tray-protrusion step $S_8$". FIG. 5 is a flowchart illustrating the sample feeding method according to the embodiment of the present disclosure. In the below, the procedure steps are described one by one.

FIG. 3 is also a schematic diagram illustrating the sequential structure of the sample feeding apparatus 1 in the sample-setting-wait step $S_1$ in the sample feeding method according to the embodiment of the present disclosure. FIG. 4 is also a schematic diagram illustrating in what state the sample feeding apparatus 1 is in the sample-setting-wait step $S_1$ in the sample feeding method according to the embodiment of the present disclosure. FIGS. 3 and 4 specifically are each a diagram illustrating the state in which the waste tray 343 is positioned at the sixth position P6.

First of all, in the sample-setting-wait step $S_1$ of FIG. 5, the sample feeding apparatus 1 waits for a user to set the sample-containing sample tube 22 to the pressure cylinder 31. At this time, with the waste tray 343 of the waste-containing cylinder 34 being at the sixth position P6, the waste tray 343 accommodates any sample remained in the pressure shell 52 so that the sample remained in the pressure shell 52 is prevented from dropping to the side of the tube holder 21, i.e., the side in the Z-axis negative direction of FIG. 4. This thus allows the user to place the sample tube 22 to the tube holder 21 with safety and ease without worrying about the sample attaching to his hands and others.

In the sample-setting-wait step $S_1$, also with the waste tray 343 being at the sixth position P6, if a cleaning agent is directed from the sample line 6 toward the waste tray 343, any sample remained in both the sample line 6 and the nozzle 51 may be removed while the cleaning agent being collected in the waste tray 343. This accordingly prevents contamination in the process of analysis, i.e., prevents a sample used for an analysis from getting in a different sample for another analysis.

2-2. Waste-Tray-Storage Step $S_2$

Figure 6:
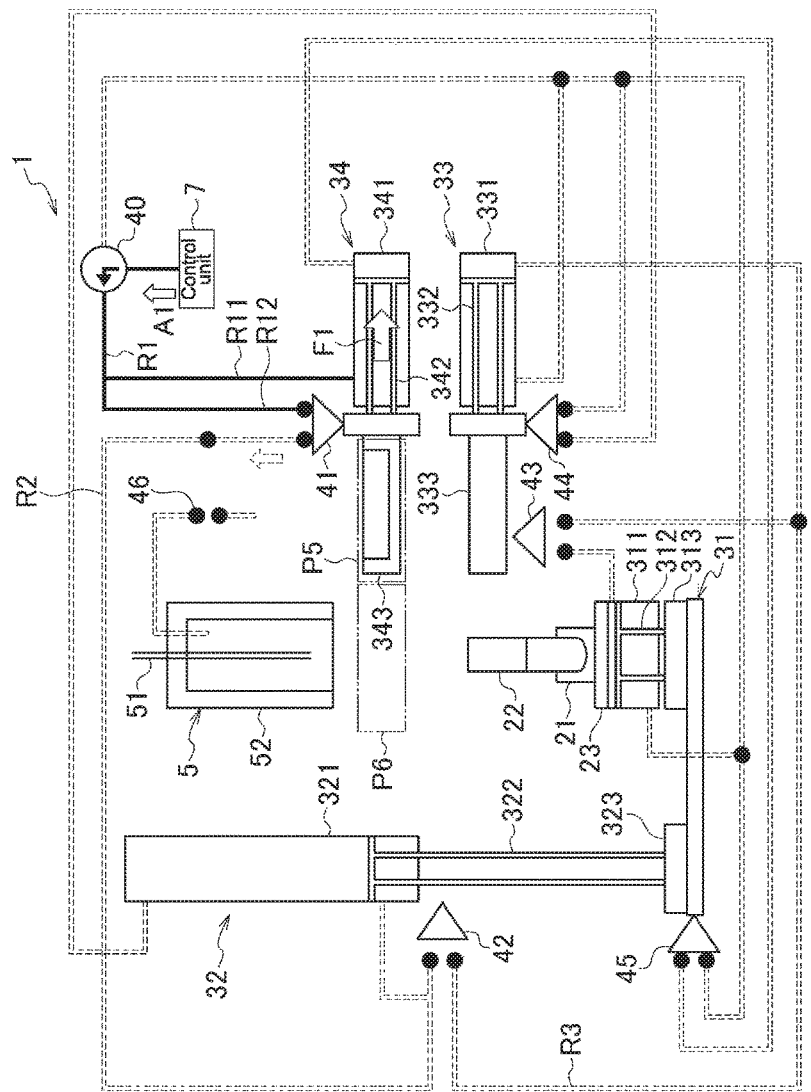
FIG. 6 is a schematic diagram illustrating the sequential structure of the sample feeding apparatus in a step $S_2$ of waste tray storage in the sample feeding method according to the embodiment of the present disclosure.
Figure 7:
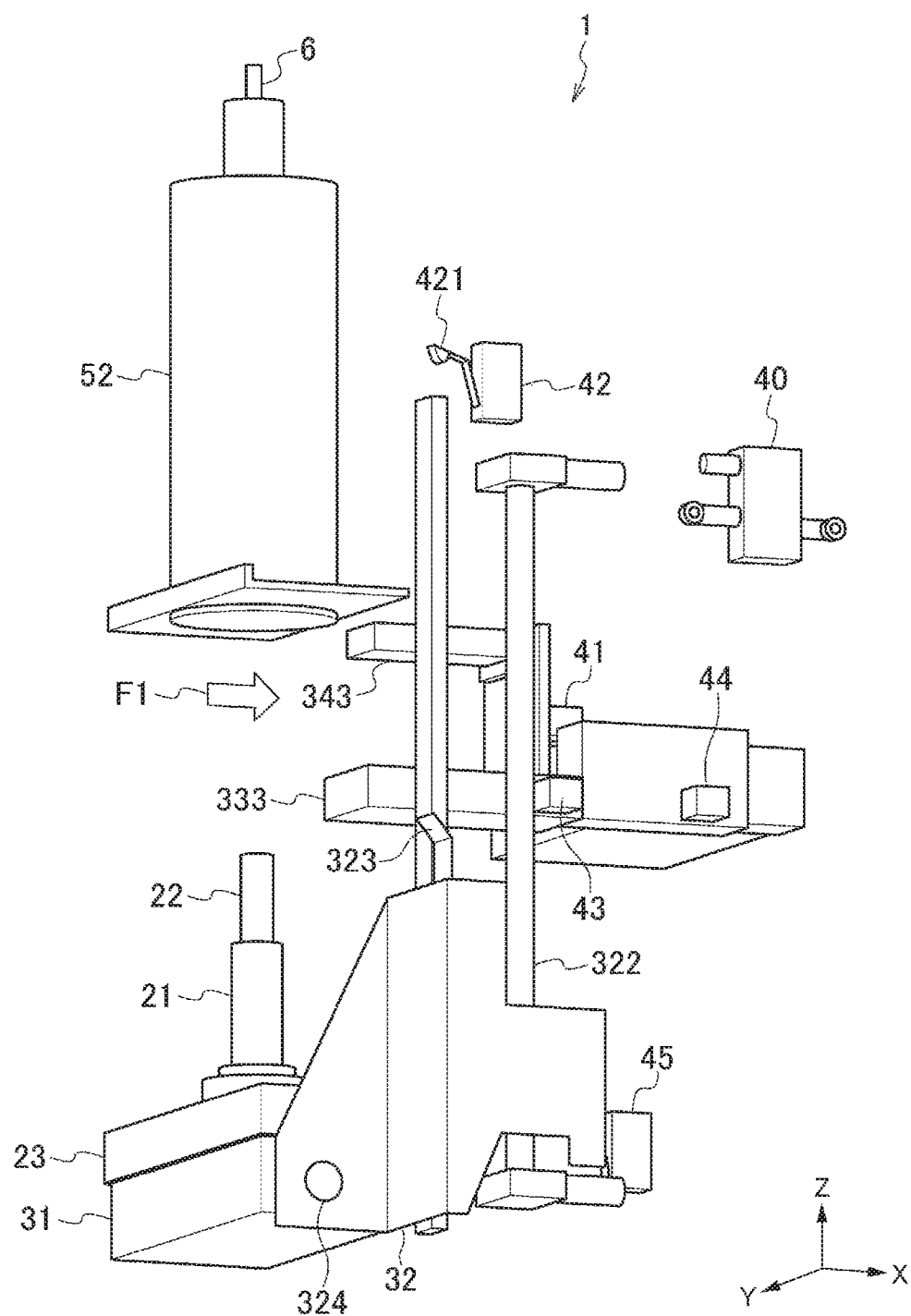
FIG. 7 is a schematic diagram illustrating in what state the sample feeding apparatus is in the waste-tray-storage step $S_2$ in the sample feeding method according to the embodiment of the present disclosure.

FIG. 6 is a schematic diagram illustrating the sequential structure of the sample feeding apparatus 1 in the waste-tray-storage step $S_2$ in the sample feeding method according to the embodiment of the present disclosure. FIG. 7 is a schematic diagram illustrating in what state the sample feeding apparatus 1 is in the waste-tray-storage step $S_2$ in the sample feeding method according to the embodiment of the present disclosure. FIGS. 6 and 7 specifically are each a diagram illustrating the state in which the waste tray 343 is positioned at the fifth position P5.

In the waste-tray-storage step $S_2$ of FIG. 5, first of all, the control unit 7 directs the gas in the direction of an arrow A1 via the electromagnetic valve 40 (see FIG. 6). The gas flows in the flow path R1, and then the flow of gas is split into two to go through the flow paths R11 and R12.

The gas flowing through the flow path R11 is injected into the waste-containing cylinder body section 341 (see FIG. 6). In response thereto, the waste-cylinder-use piston 342 is moved in the direction of an arrow F1, i.e., in the Y-axis negative direction, and the waste tray 343 is moved from the sixth position P6 to the fifth position P5 for storage (see FIGS. 6 and 7). Accordingly, the mechanical valve 41 physically opens itself.

The gas flowing through the flow path R12 is directed toward the mechanical valve 41. This allows the gas to flow through the flow path R2.

The gas injection by the control unit 7 is not specifically restricted, but may be automatically performed in the sample-setting-wait step $S_1$ by detection of the sample tube 22 when it is set to the tube holder 21, for example. Alternatively, the control unit 7 may perform the gas injection by the user manually operating the apparatus 1. Herein, the gas is not specifically restricted, but is exemplified by air.

With the waste tray 343 moving to the fifth position P5, the shell cylinder 31 is allowed to move toward the pressure shell 52 in the pressure-cylinder-moving-up step $S_3$ that will be described later.

2-3. Pressure-Cylinder-Moving-Up Step $S_3$

Figure 8:
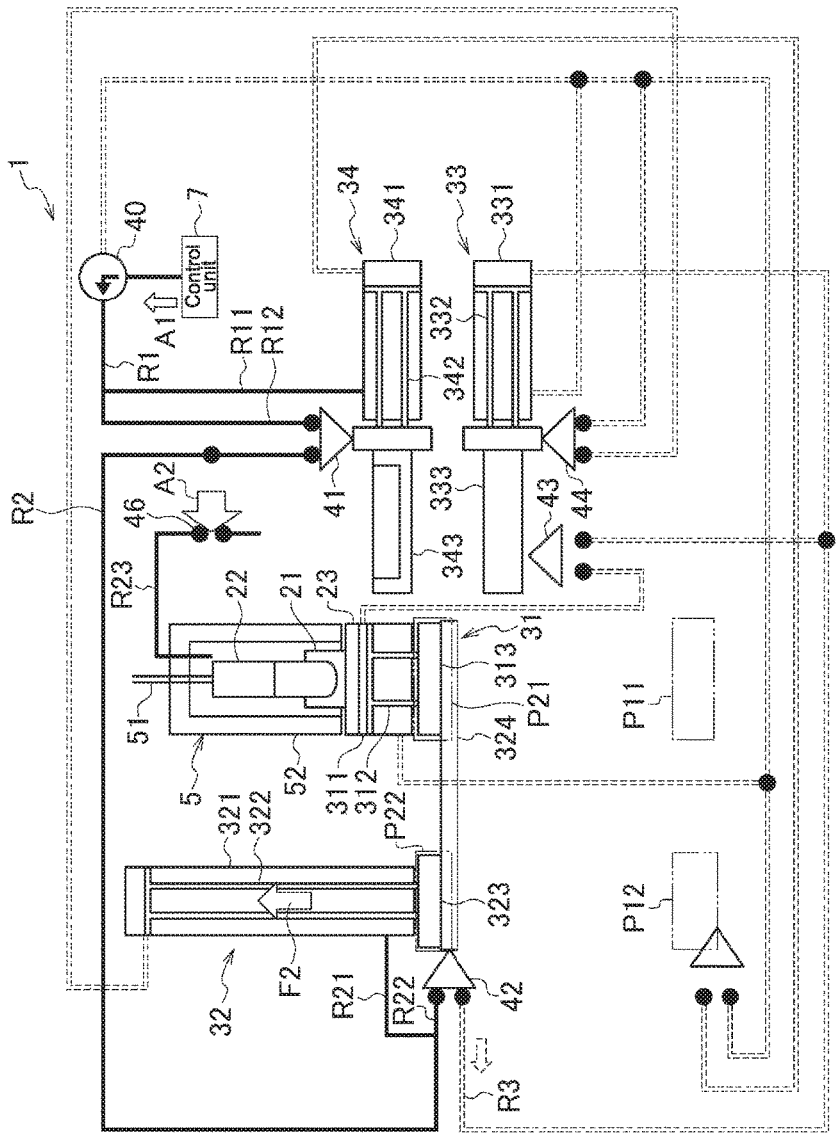
FIG. 8 is a schematic diagram illustrating the sequential structure of the sample feeding apparatus in a step $S_3$ of pressure cylinder moving up in the sample feeding method according to the embodiment of the present disclosure.
Figure 9:
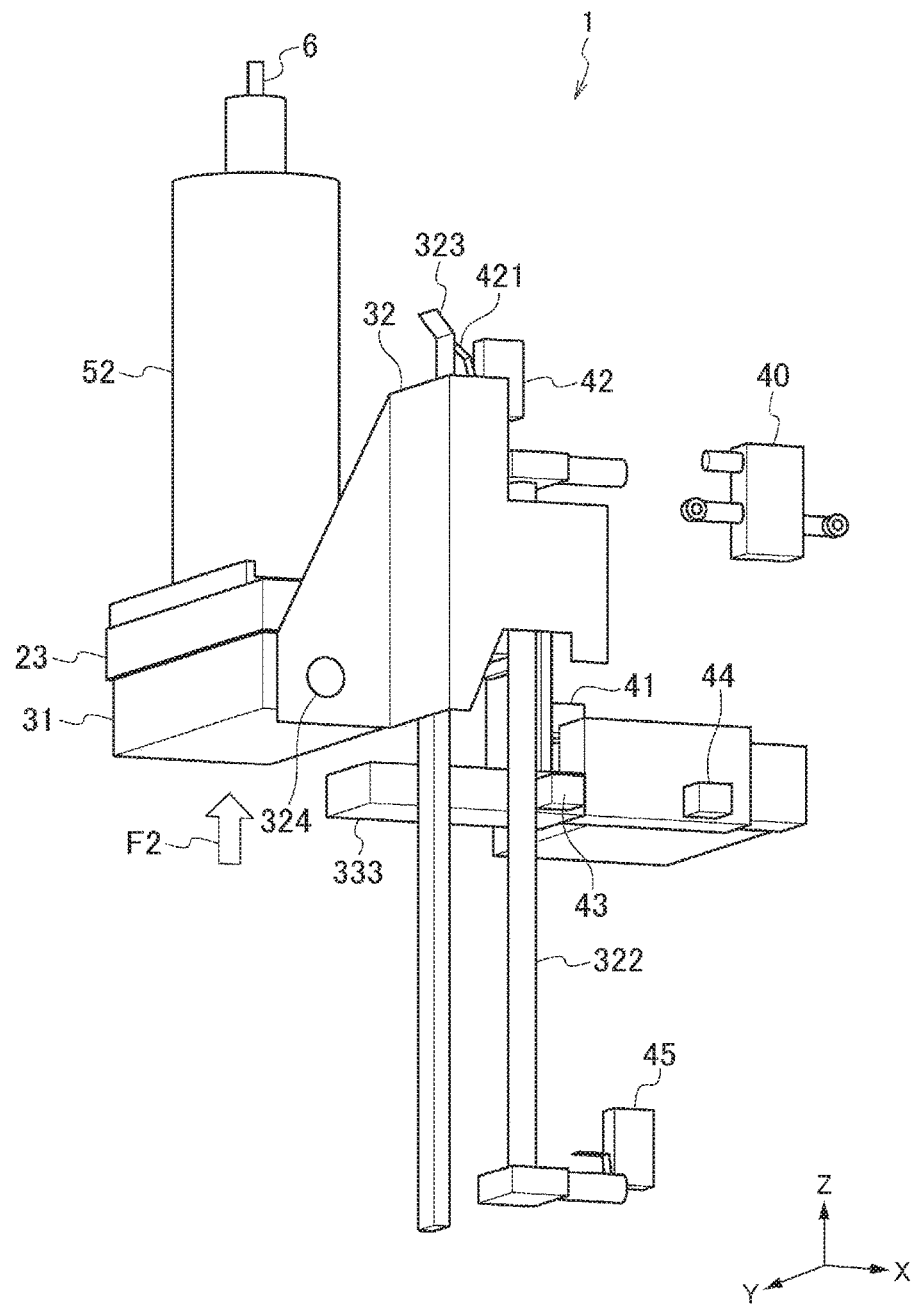
FIG. 9 is a schematic diagram illustrating in what state the sample feeding apparatus is in the pressure-cylinder-moving-up step $S_3$ in the sample feeding method according to the embodiment of the present disclosure.

FIG. 8 is a schematic diagram illustrating the sequential structure of the sample feeding apparatus 1 in the pressure-cylinder-moving-up step $S_3$ in the sample feeding method according to the embodiment of the present disclosure. FIG. 9 is a schematic diagram illustrating in what state the sample feeding apparatus 1 is in the pressure-cylinder-moving-up step $S_3$ in the sample feeding method according to the embodiment of the present disclosure. FIGS. 8 and 9 specifically are each a diagram illustrating the state in which both the up-and-down-cylinder-use leg section 323 and the pressure-cylinder-use leg section 313 are positioned at the second positions P21 and P22.

In the pressure-cylinder-moving-up step $S_3$ of FIG. 5, first of all, the flow of gas directed through the flow path R2 in the waste-tray-storage step $S_2$ described above is split into two to go through the flow paths R21 and R22 (see FIG. 8). The gas flowing through the flow path R21 is injected into the up-and-down cylinder body section 321. Then in this step $S_3$, the up-and-down-cylinder-use piston 322 is moved in the direction of an arrow F2, i.e., in the Z-axis positive direction, so that the up-and-down-cylinder-use leg section 323 is moved from the first position P12 to the second position P22 (see FIGS. 8 and 9). Accordingly, in this step $S_3$, the mechanical valve 42 opens itself so that the gas in the flow path R22 is allowed to go through the flow path R3 (see FIG. 8).

Also in this step $S_3$, the pressure-cylinder-use leg section 313 is also moved from the first position P11 to the second position P21 so that the sample tube 22 is sealed in the pressure shell 52.

Also in this step $S_3$, in response to the flow of gas in the flow path R2, the air-operated valve 46 is opened, and the gas is injected into the pressure shell 52 via the flow path R23 (arrow A2 of FIG. 8).

2-4. Support-Arm-Protrusion Step $S_4$

Figure 10:
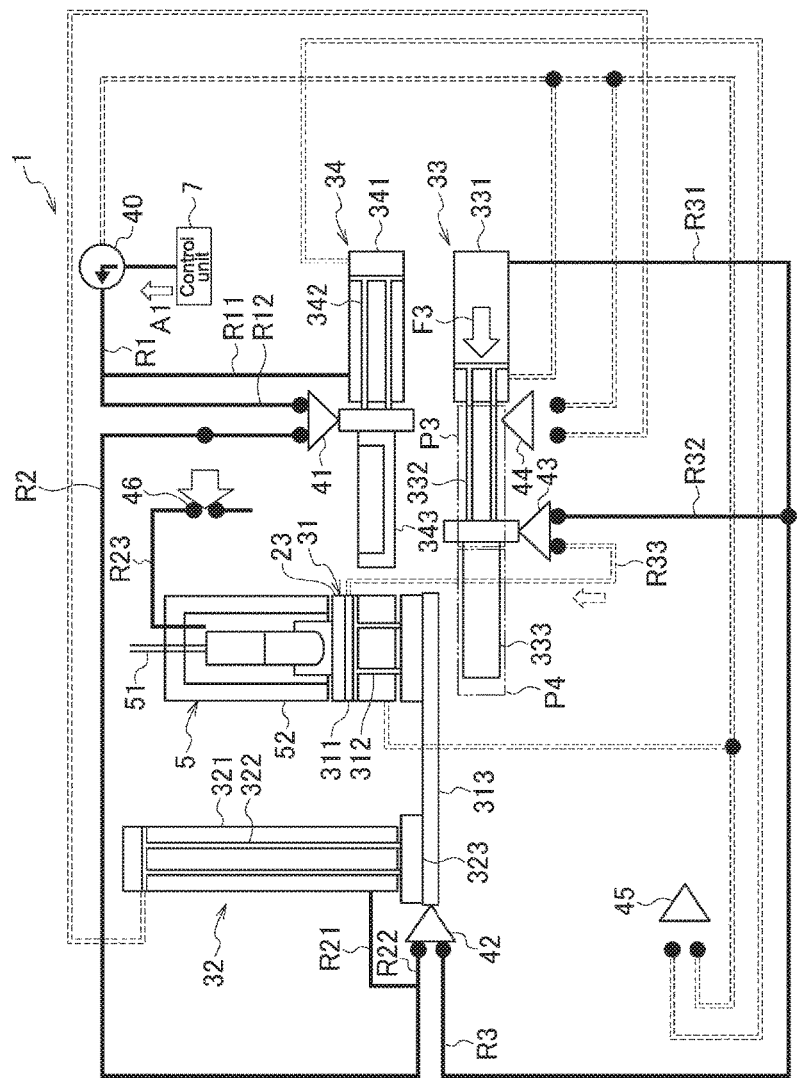
FIG. 10 is a schematic diagram illustrating the sequential structure of the sample feeding apparatus in a step $S_4$ of support arm protrusion in the sample feeding method according to the embodiment of the present disclosure.
Figure 11:
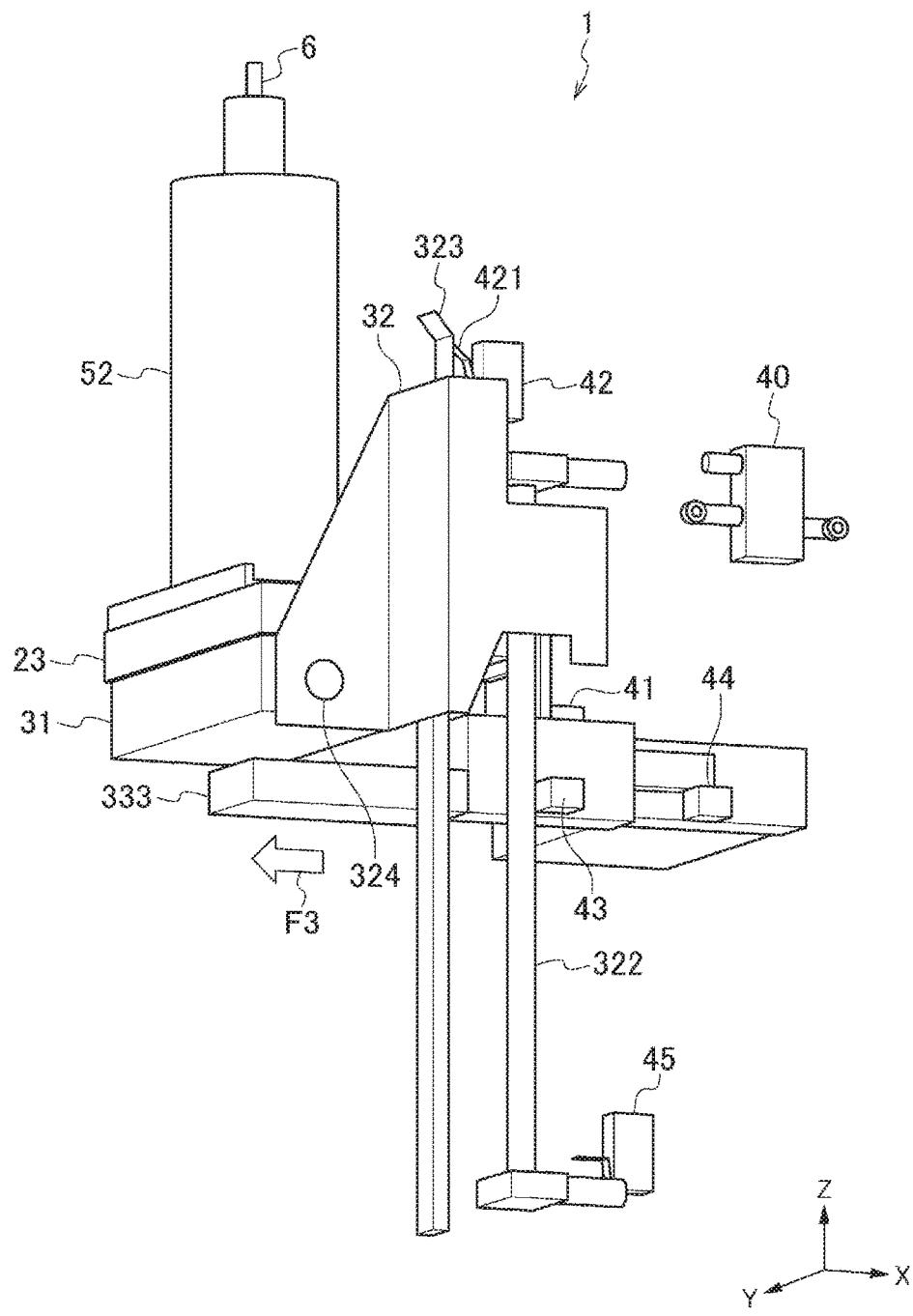
FIG. 11 is a schematic diagram illustrating in what state the sample feeding apparatus is in the support-arm-protrusion step $S_4$ in the sample feeding method according to the embodiment of the present disclosure.

FIG. 10 is a schematic diagram illustrating the sequential structure of the sample feeding apparatus 1 in the support-arm-protrusion step $S_4$ in the sample feeding method according to the embodiment of the present disclosure. FIG. 11 is a schematic diagram illustrating in what state the sample feeding apparatus 1 is in the support-arm-protrusion step $S_4$ in the sample feeding method according to the embodiment of the present disclosure. FIGS. 10 and 11 specifically are each a diagram illustrating the state in which the support arm 333 is positioned at the fourth position P4.

In the support-arm-protrusion step $S_4$ of FIG. 5, the flow of gas directed into the flow path R3 in the pressure-cylinder-moving-up step $S_3$ described above is split into two to go through the flow paths R31 and R32 (see FIG. 10). The gas flowing through the flow path R31 is injected into the support cylinder body section 331. Then in this step $S_4$, the support-cylinder-use piston 332 is moved in the direction of an arrow F3, i.e., in the Y-axis positive direction, so that the support arm 333 is moved from the third position P3 to the fourth position P4, and is protruded (see FIGS. 10 and 11). Accordingly, in this step $S_4$, the mechanical valve 43 opens itself so that the gas in the flow path R32 is allowed to go through the flow path R33.

2-5. Sample-Feeding Step $S_5$

Figure 12:
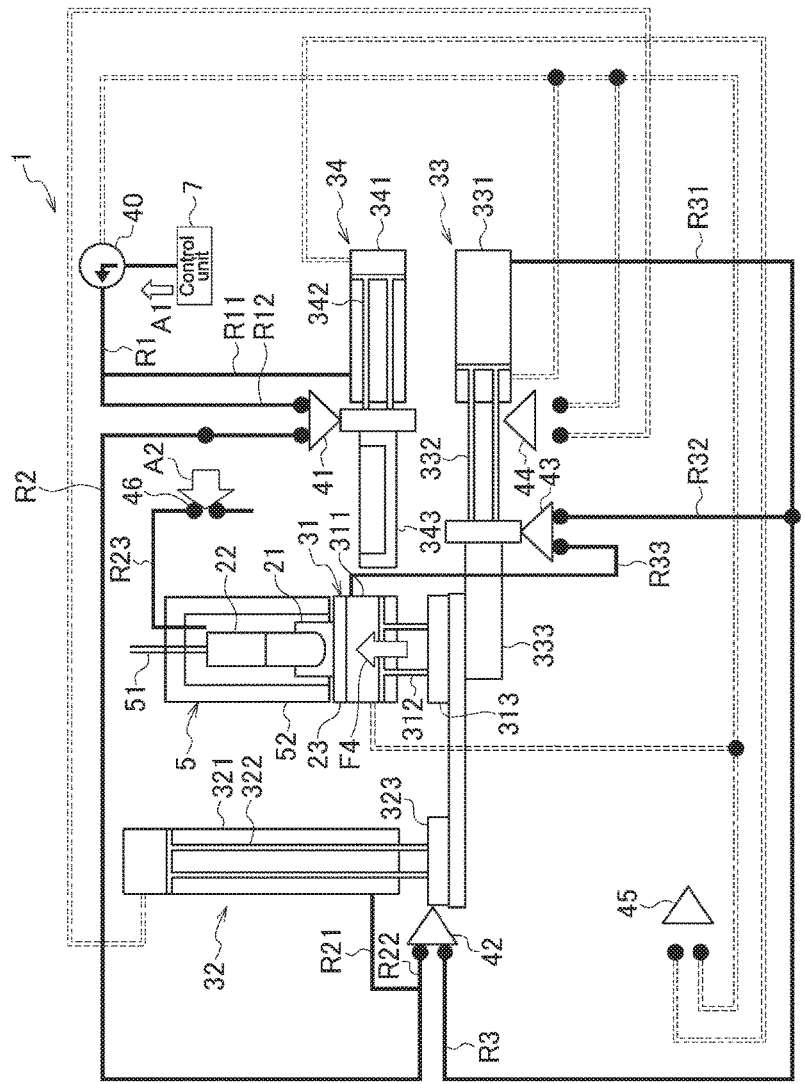
FIG. 12 is a schematic diagram illustrating the sequential structure of the sample feeding apparatus in a step $S_5$ of sample feeding in the sample feeding method according to the embodiment of the present disclosure.
Figure 13:
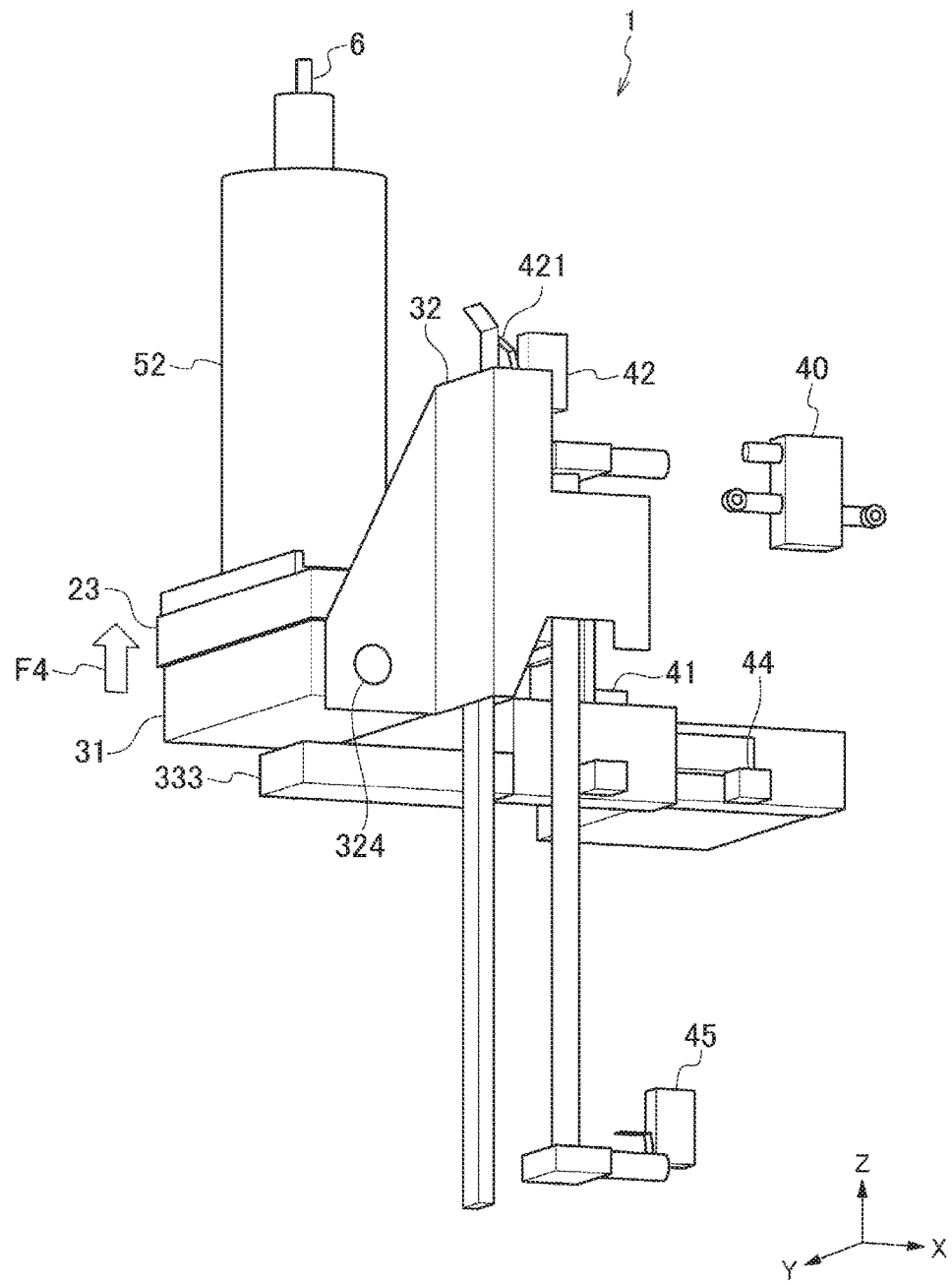
FIG. 13 is a schematic diagram illustrating in what state the sample feeding apparatus is in the sample-feeding step $S_5$ in the sample feeding method according to the embodiment of the present disclosure.

FIG. 12 is a schematic diagram illustrating the sequential structure of the sample feeding apparatus 1 in the sample-feeding step $S_5$ in the sample feeding method according to the embodiment of the present disclosure. FIG. 13 is a schematic diagram illustrating in what state the sample feeding apparatus 1 is in the sample-feeding step $S_5$ in the sample feeding method according to the embodiment of the present disclosure. FIGS. 12 and 13 specifically are each a diagram illustrating the state in which the sample is directed to the micro-sized particle measurement apparatus 100 with pressure application.

In the sample-feeding step $S_5$ of FIG. 5, feeding of a sample is started toward the micro-sized particle measurement apparatus 100 (flow cytometer), for example (see FIG. 1 again). In this step $S_5$, first of all, the gas directed into the flow path R33 in the support-arm-protrusion step $S_4$ described above is injected into the pressure cylinder body section 311 (see FIG. 12). In response thereto, both the pressure-cylinder-use piston 312 and the pressure-cylinder-use leg section 313 are moved to the side in the Z-axis negative direction of FIG. 13. Herein, with the sample feeding apparatus 1 according to the embodiment of the present disclosure, the pressure-cylinder-use leg section 313 and the up-and-down-cylinder-use leg section 323 in the state of FIGS. 12 and 13 are assumed to be within the range of the second positions P21 and 22, respectively. With such positioning, the coupling section 324 comes in contact with the support arm 333, and the support arm 333 supports the pressure cylinder 31. The pressure cylinder 31 is thus allowed to apply pressure into the pressure shell 52 in the direction of an arrow F4, i.e., in the Z-axis positive direction (see FIGS. 12 and 13).

The gas passed through the flow path R23 is injected into the pressure shell 52. As such, the tube holder 21 is put under pressure by the pressure cylinder 31 in the pressure shell 52, and in the gas-tight state, the sample drawn out from the nozzle 51 is fed to the micro-sized particle measurement apparatus 100 via the sample line 6.

As described above, for the sample feeding, the sample feeding apparatus 1 moves up and down the sample tube by using both the up-and-down cylinder 32 for the up-and-down movement of the sample tube, and the pressure cylinder 31 for the pressure application thereto. Therefore, irrespective of the application of high pressure, the user may operate the sample feeding apparatus 1 with no worry about getting his fingers caught in the cylinder and others, damaging the sample tube, and causing biological hazards, for example. That is, with the sample feeding apparatus 1, the user may perform sample feeding with safety and ease.

2-6. Pressure-Cylinder-Release Step $S_6$

Figure 14:
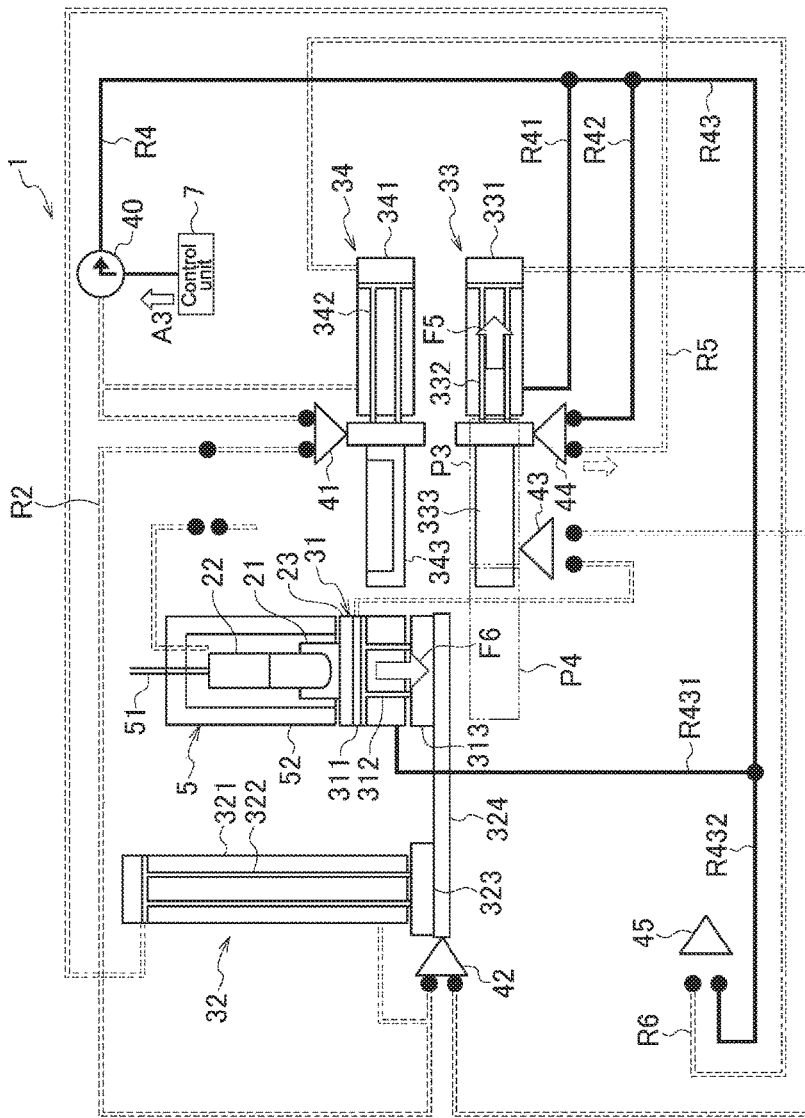
FIG. 14 is a schematic diagram illustrating the sequential structure of the sample feeding apparatus in a step $S_6$ of pressure cylinder release in the sample feeding method according to the embodiment of the present disclosure.
Figure 15:
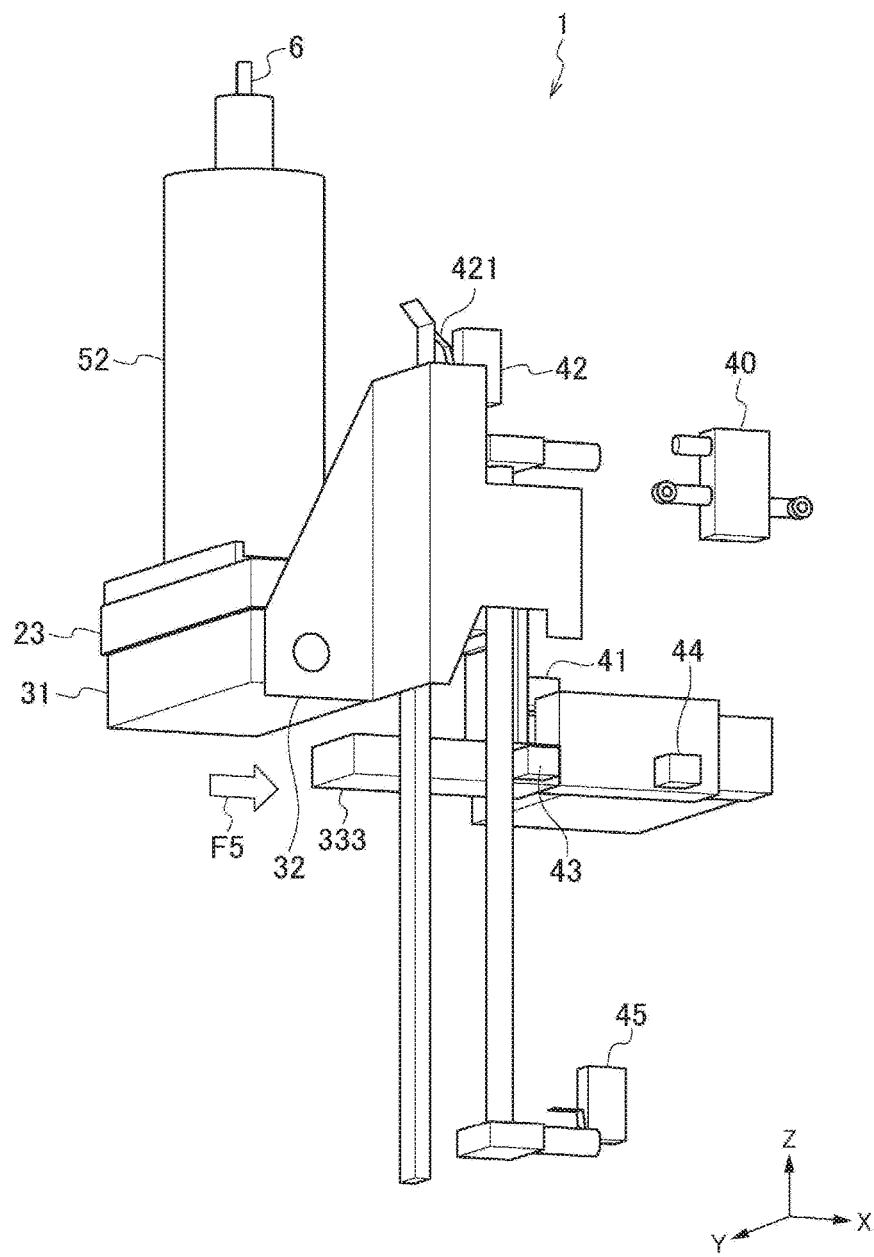
FIG. 15 is a schematic diagram illustrating in what state the sample feeding apparatus is in the pressure-cylinder-release step $S_6$ in the sample feeding method according to the embodiment of the present disclosure.

FIG. 14 is a schematic diagram illustrating the sequential structure of the sample feeding apparatus 1 in the pressure-cylinder-release step $S_6$ in the sample feeding method according to the embodiment of the present disclosure. FIG. 15 is a schematic diagram illustrating in what state the sample feeding apparatus 1 is in the pressure-cylinder-release step $S_6$ in the sample feeding method according to the embodiment of the present disclosure. FIGS. 14 and 15 specifically are each a diagram illustrating the state in which the support arm 333 is positioned at the third position P3.

In the pressure-cylinder-release step $S_6$ of FIG. 5, the control unit 7 directs the gas in the direction of an arrow A3 (see FIG. 14) via the electromagnetic valve 40. The flow of gas is directed through the flow path R4, and then is split into two to go through the flow paths R42 and R43.

In this step $S_6$, the gas flowing through the flow path R41 is injected into the support cylinder body section 331 (see FIG. 14). In response thereto, the support-cylinder-use piston 332 is moved in the direction of an arrow F5, i.e., in the Y-axis negative direction, so that the support arm 333 is moved from the fourth position P4 to the third position P3 (see FIGS. 14 and 15). Accordingly, in this step $S_6$, the mechanical valve 44 physically opens itself.

Also in this step $S_6$, the gas flowing through the flow path R42 is directed toward the mechanical valve 44. Accordingly, in this step $S_6$, the gas in the flow path R42 is allowed to go through the flow path R5.

Also in this step $S_6$, the flow of gas flowing through the flow path R43 is split into two to go through the flow paths R431 and R432. The gas flowing through the flow path R431 is injected into the pressure cylinder body section 311. Accordingly, both the pressure-cylinder-use piston 312 and the pressure-cylinder-use leg section 313 are moved to the side of the pressure feeding section 5. Herein, the pressure cylinder 313 is moved within the range of the second position P21. Therefore, in this step $S_6$, the pressure application by the pressure cylinder 31 is performed in the direction of an arrow F6, i.e., in the Z-axis negative direction, so that the pressure in the pressure shell 52 by the pressure cylinder 31 is released (see FIGS. 14 and 15).

2-7. Pressure-Cylinder-Moving-Down Step $S_7$

Figure 16:
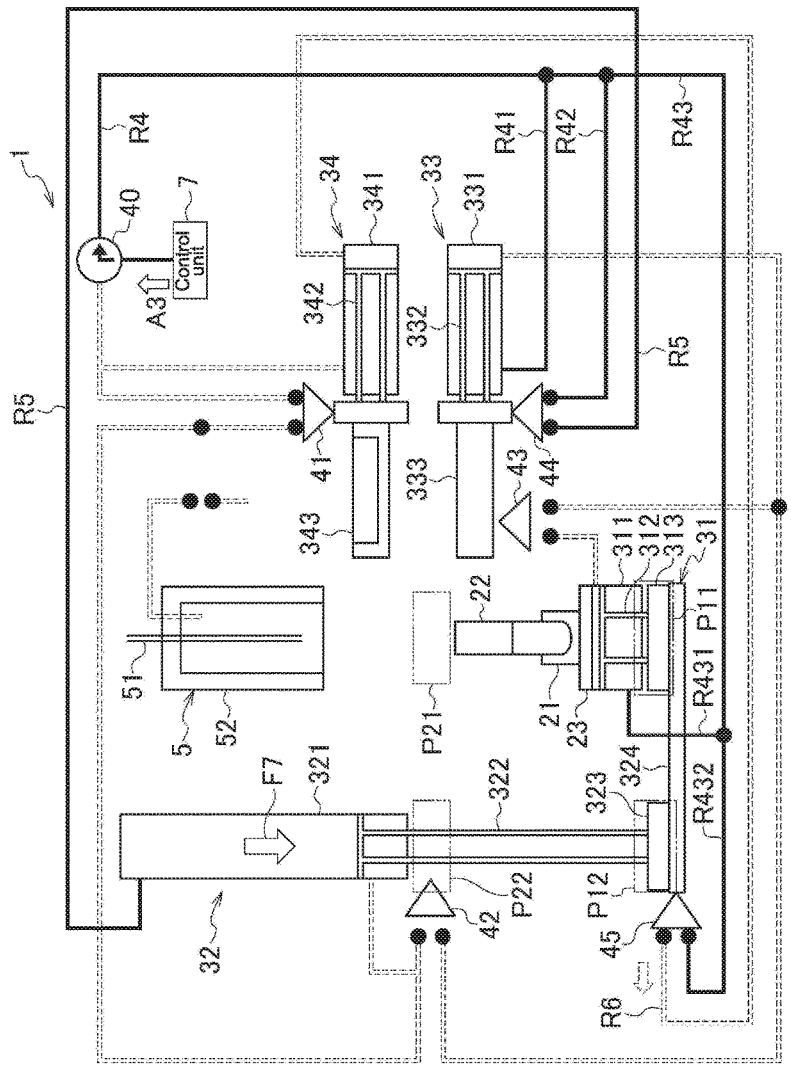
FIG. 16 is a schematic diagram illustrating the sequential structure of the sample feeding apparatus in a step $S_7$ of pressure cylinder moving down in the sample feeding method according to the embodiment of the present disclosure.
Figure 17:
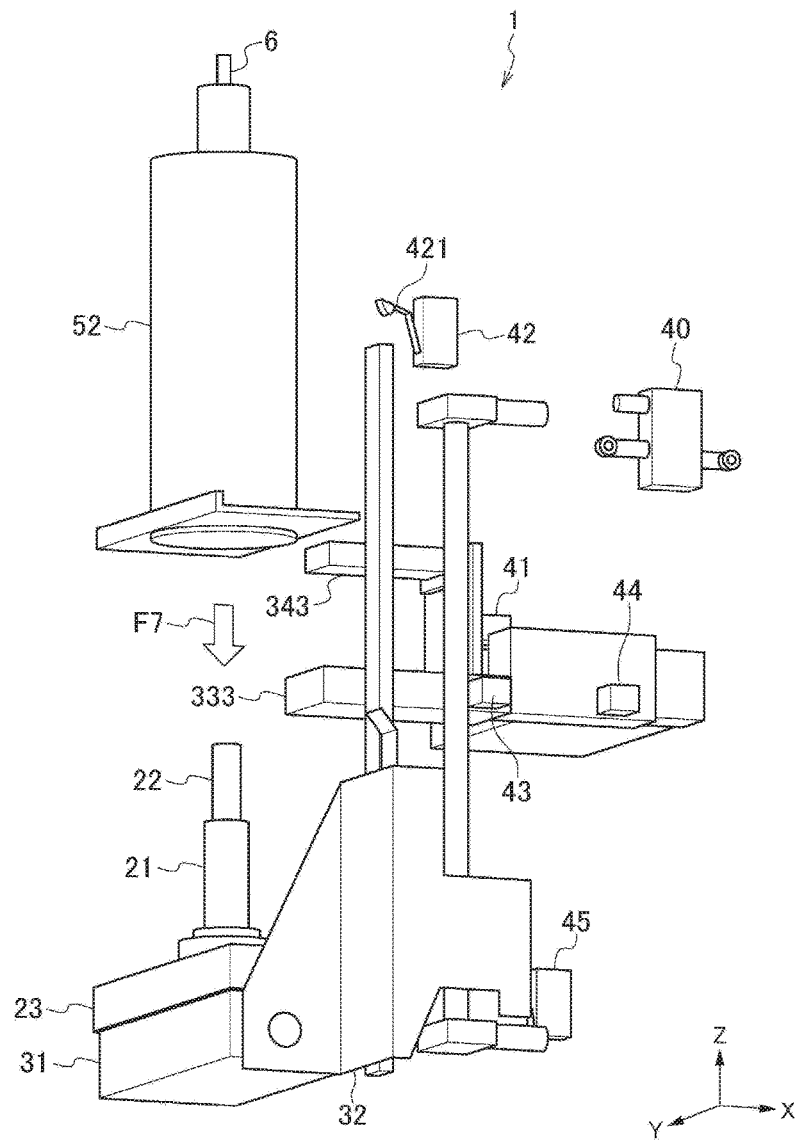
FIG. 17 is a schematic diagram illustrating in what state the sample feeding apparatus is in the pressure-cylinder-moving-down step $S_7$ in the sample feeding method according to the embodiment of the present disclosure.

FIG. 16 is a schematic diagram illustrating the sequential structure of the sample feeding apparatus 1 in the pressure-cylinder-moving-down step $S_7$ in the sample feeding method according to the embodiment of the present disclosure. FIG. 17 is a schematic diagram illustrating in what state the sample feeding apparatus 1 is in the pressure-cylinder-moving-down step $S_7$ in the sample feeding method according to the embodiment of the present disclosure. FIGS. 16 and 17 specifically are each a diagram illustrating the state in which both the up-and-down-cylinder-use leg section 323 and the pressure-cylinder-use leg section 313 are positioned at the first positions P11 and P12.

In the pressure-cylinder-moving-down step $S_7$ of FIG. 5, the gas directed into the flow path R5 in the pressurecylinder-release step $S_6$ described above is injected into the up-and-down cylinder body section 321. Then in this step $S_7$, the up-and-down-cylinder-use piston 322 is moved in the direction of an arrow F7, i.e., in the Z-axis negative direction, so that the up-and-down-cylinder-use leg section 323 is moved from the second position P22 to the first position P11 (see FIGS. 16 and 17). Accordingly, in this step $S_7$, the mechanical valve 45 opens itself, and the gas in the flow path R432 is allowed to flow through the flow path R6.

In this step $S_7$, the pressure-cylinder-use leg section 313 is also moved from the second position P21 to the first position P11. This thus allows the sample tube 22 to be removed from the tube holder 21 after the sample feeding to the micro-sized particle measurement apparatus 100.

2-8. Waste-Tray-Protrusion Step $S_8$

Figure 18:
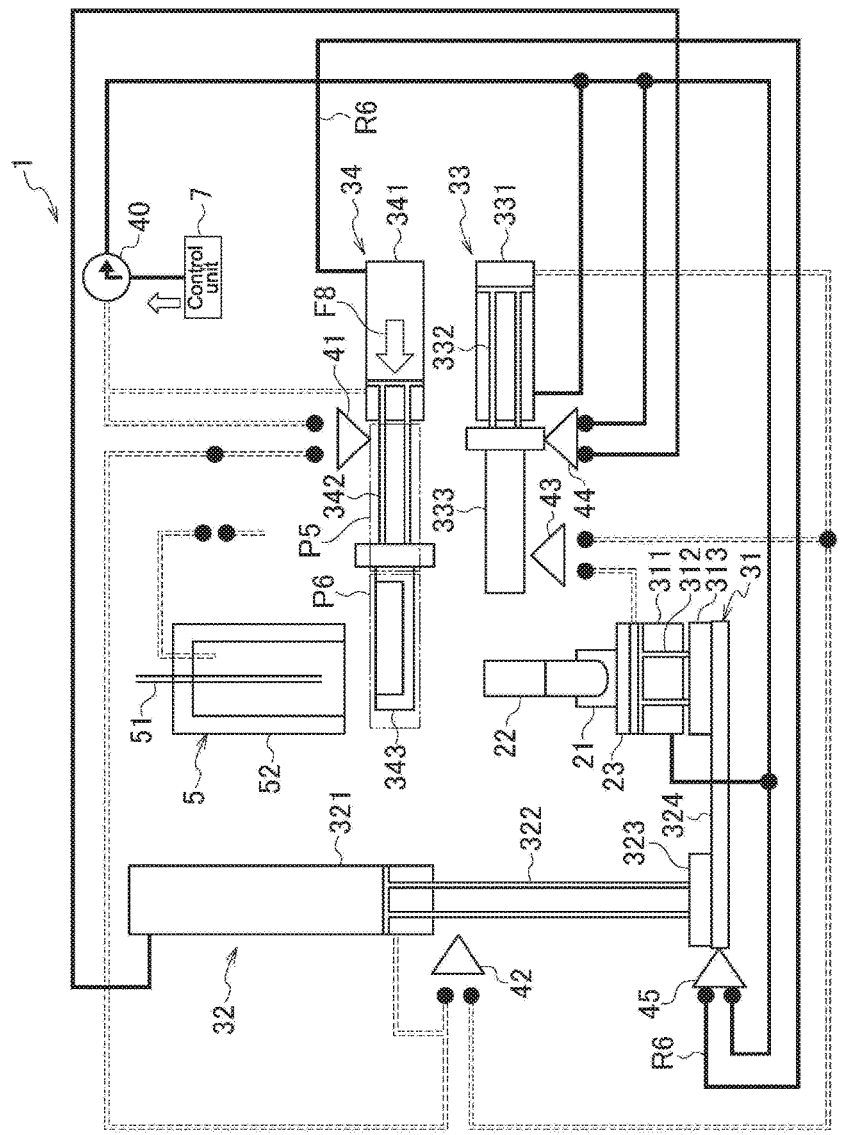
FIG. 18 is a schematic diagram illustrating the sequential structure of the sample feeding apparatus in a step $S_8$ of waste tray protrusion in the sample feeding method according to the embodiment of the present disclosure.
Figure 19:
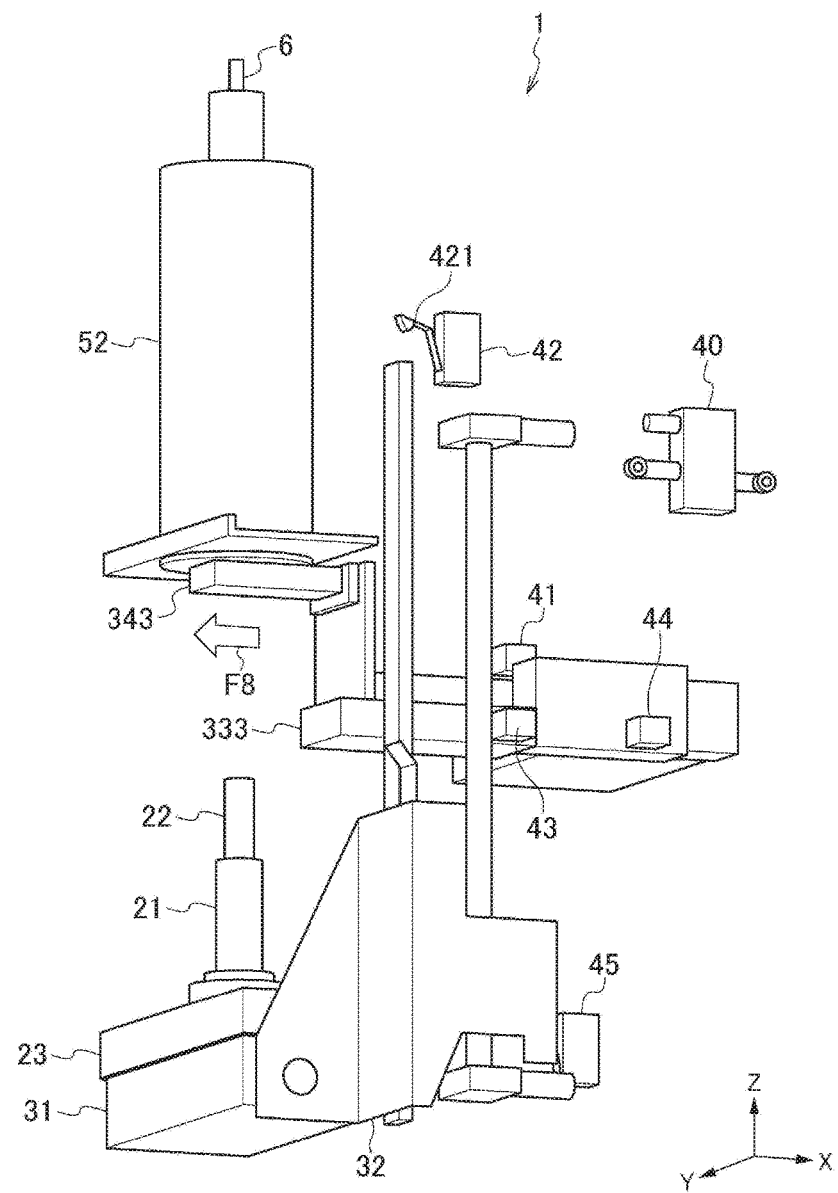
FIG. 19 is a schematic diagram illustrating in what state the sample feeding apparatus is in the waste-tray-protrusion step $S_8$ in the sample feeding method according to the embodiment of the present disclosure.

FIG. 18 is a schematic diagram illustrating the sequential structure of the sample feeding apparatus 1 in the waste-tray-protrusion step $S_8$ in the sample feeding method according to the embodiment of the present disclosure. FIG. 19 is a schematic diagram illustrating in what state the sample feeding apparatus 1 is in the waste-tray-protrusion step $S_8$ in the sample feeding method according to the embodiment of the present disclosure. FIGS. 18 and 19 specifically are each a diagram illustrating the state in which the waste tray 343 is positioned at the sixth position P6.

In the waste-tray-protrusion step $S_8$ of FIG. 5, the gas passed through the flow path R6 in the pressure-cylinder-moving-down step $S_7$ described above is injected into the waste-containing cylinder body section 341. Then in this step $S_8$, the waste-cylinder-use piston 342 is moved in the direction of an arrow F8, i.e., in the Y-axis positive direction, so that the up-and-down-cylinder-use leg section 343 is moved from the fifth position P5 to the sixth position P6 (see FIGS. 18 and 19). At this time, with the waste tray 343 of the waste-containing cylinder 34 being positioned at the sixth position P6, the waste tray 343 may accommodate any sample remained in the pressure shell 52 so that the sample remained in the pressure shell 52 is prevented from dropping to the side of the tube holder 21, i.e., the side in the Z-axis negative direction of FIG. 19. This thus allows the user to remove the sample tube 22 from the tube holder 21 with safety and ease without worrying about the sample attaching to his hands and others.

In the sample-setting-wait step $S_1$, also with the waste tray 343 being at the sixth position P6, if a cleaning agent is directed from the sample line 6 toward the waste tray 343, any sample remained in both the sample line 6 and the nozzle 51 may be removed while the cleaning agent being collected in the waste tray 343. This accordingly prevents contamination in the process of analysis, i.e., prevents a sample used for an analysis from getting in a different sample for another analysis.

As described above, the sample feeding apparatus 1 according to the embodiment of the present disclosure uses both the pressure cylinder 31 and the up-and-down cylinder 32. Therefore, even if the pressure cylinder 31 in use is a large-sized air cylinder, for example, the force to be applied to the pressure cylinder 31 is to be controlled so that the user is protected not to get his fingers caught in the cylinder and others, or the sample tube is protected from damage. This thus ensures the safety during the sample feeding with pressure application.

Further, with the pressure cylinder 31 being supported by the support arm 333 during sample feeding with pressure application, the sample feeding is performed with more safety.

Still further, with the sample feeding apparatus 1, the control unit 7 operates only when the gas is forwarded via the electromagnetic valve 40, and the cylinders mainly operate under the physical control by the mechanical valves 41 to 45. Accordingly, the user is allowed to use the sample feeding apparatus 1 without worrying about any possible abnormal conditions of the system therein.

Still further, when the user places the sample tube 22 to the tube holder 21, and when the user removes the sample tube 22 from the tube holder 21, the waste tray 343 collects any waste remained in the pressure shell 52. Accordingly, the user is allowed to use the apparatus with safety without worrying about the waste attaching to his hands and others.

The sample feeding apparatus according to the embodiment of the present disclosure may be also in the following structures.

(1) A sample feeding apparatus, including:
 a first cylinder configured to be mounted with a sample tube;
 a second cylinder configured to move the first cylinder between a first position and a second position, the first position being for mounting of the sample tube, the second position being for feeding of a sample in the sample tube; and
 a sealing section configured to cover the sample tube, the sample tube being mounted to the first cylinder being at the second position, the first cylinder applying pressure to an inner space of the sealing section at the second position.

(2) The sample feeding apparatus according to (1), further including
 a third cylinder configured to be mounted to support the first cylinder in a state that the first cylinder is positioned at the second position.

(3) The sample feeding apparatus according to (2), in which
 the third cylinder is configured to support the first cylinder by moving from a third position to a fourth position, the third position allowing the first cylinder to move between the first position and the second position, the fourth position being on an opposite side of the sealing section with respect to the first cylinder.

(4) The sample feeding apparatus according to any one of (1) to (3), further including
 a fourth cylinder configured to be mounted to accommodate any of the sample remained in the sealing section in a state that the first cylinder is positioned at the first position.

(5) The sample feeding apparatus according to (4), in which
 the fourth cylinder is configured to accommodate the sample remained in the sealing section by moving from a fifth position to a sixth position, the fifth position allowing the first cylinder to move between the first position and the second position, the sixth position being on an insertion side of the sample tube with respect to the sealing section.

(6) The sample feeding apparatus according to (5), in which
 each of the first cylinder, the second cylinder, the third cylinder, and the fourth cylinder includes
  a flow path that is configured to move gas for injection into the cylinder, and
  a valve that is configured to draw in and out the gas in the other cylinders via the flow path based on an operation of the cylinder.

(7) The sample feeding apparatus according to (6), further including
 a control unit configured to inject the gas into the fourth cylinder, in which
  the fourth cylinder includes
  a first valve that is configured to physically open itself in response to the fourth cylinder moving from the sixth position to the fifth position by the injection of the gas thereinto, and to allow the gas to be injected into the second cylinder to move the second cylinder from the first position to the second position.

(8) The sample feeding apparatus according to (7), in which the sealing section is configured to allow the injection of the gas into the inner space thereof by the opening of the first valve.

(9) The sample feeding apparatus according to (7) or (8), in which
the second cylinder includes
a second valve that is configured to physically open itself to allow the gas to be injected into the third cylinder in a state that the second cylinder is positioned at the second position, and to allow the third cylinder to move from the third position to the fourth position.

(10) The sample feeding apparatus according to (9), in which
the third cylinder includes
a third valve that is configured to physically open itself to allow the gas to be injected into the first cylinder in a state that the third cylinder is positioned at the fourth position, and to allow the first cylinder to apply pressure into the sealing section at the second position.

(11) The sample feeding apparatus according to (10), in which
the control unit is configured to perform the injection of the gas into the first cylinder and the third cylinder, and
the third cylinder includes
a fourth valve that is configured to physically open itself in response to the third cylinder moving from the fourth position to the third position by the injection of the gas thereinto, and to allow the second cylinder to move from the second position to the first position.

(12) The sample feeding apparatus according to (11), in which
by the control unit injecting the gas into the first cylinder, the pressure applied by the first cylinder into the sealing section is released.

(13) The sample feeding apparatus according to (12), in which
the second cylinder includes
a fifth valve that is configured to physically open itself to allow the gas to be injected into the fourth cylinder in a state that the second cylinder is positioned at the first position, and to allow the fourth cylinder to move from the fifth position to the sixth position.

(14) The sample feeding apparatus according to any one of (1) to (13), in which
the sealing section is attached with a sample line that is configured to feed the sample in the sample tube to an outside.

(15) A flow cytometer coupled with the sample feeding apparatus according to any one of (1) to (14).

(16) A sample feeding method for a sample feeding apparatus, the method including:
moving a first cylinder that is mounted with a sample tube at a first position to a second position at which a sealing section covers over the first cylinder by using a second cylinder; and
applying pressure to an inner space of the sealing section by the first cylinder.

(17) The sample feeding method according to (16), further including
supporting, in a state that the first cylinder is positioned at the second position, the first cylinder by moving a third cylinder from a third position to a fourth position, the third position allowing the first cylinder to move between the first position and the second position, the fourth position being on an opposite side of the sealing section with respect to the first cylinder.

(18) The sample feeding method according to (17), further including
using the second cylinder to move the first cylinder from the second position to the first position.

(19) The sample feeding method according to (18), further including
accommodating, in a state that the first cylinder is positioned at the first position, any of the sample remained in the sealing section by moving a fourth cylinder from a fifth position to a sixth position, the fifth position allowing the first cylinder to move between the first position and the second position, the sixth position being on an insertion side of the sample tube with respect to the sealing section.

(20) The sample feeding method according to (18) or (19), further including
starting an operation of each of the first cylinder, the second cylinder, the third cylinder, and the fourth cylinder in response to a gas flow via a flow path to the other cylinders by opening of a valve based on the operation of each of the cylinders.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A sample feeding apparatus, comprising:
a frame;
a sample tube unit including a sample holder coupled to the frame, the sample holder configured to support a sample tube;
a pressure mechanism coupled to the sample tube unit;
a moving mechanism coupled to the pressure mechanism by a coupling section, the moving mechanism configured to move both the sample tube unit and the pressure mechanism between a first position and a second position;
a housing coupled to the frame, the housing including a housing opening and an inner space that can house at least portions of the sample tube unit,
wherein the first position of the sample tube unit is a position where the sample tube unit is not enclosed by the housing,
wherein the second position of the sample tube unit is a position where the sample tube unit seals the housing opening to house at least a portion of the sample tube unit in the inner space, and
wherein the pressure mechanism is configured to apply pressure to the sample tube unit against the housing when the sample tube unit is in the second position.

2. The sample feeding apparatus according to claim 1, further comprising a support mechanism including a support arm configured to support the pressure mechanism when the pressure mechanism is in the second position.

3. The sample feeding apparatus according to claim 2, wherein the support mechanism is configured to move from a third position to a fourth position, the third position of the support mechanism is a position that does not restrict the pressure mechanism from moving between the first position and the second position, and the fourth position of the support mechanism is a position that allows the support arm of the support mechanism to support the pressure mechanism thereon.

4. The sample feeding apparatus according to claim 3, further comprising
   a waste containing mechanism coupled to the frame and configured to accommodate any of a sample remaining in the housing when the pressure mechanism is positioned at the first position.

\* \* \* \* \*